United States Patent [19]

Muchowski et al.

[11] 4,087,539
[45] May 2, 1978

[54] 5-(2-FUROYL)-, 5-(2-THENOYL)-, 5-(3-FUROYL)- AND 5-(3-THENOYL)-1,2-DIHYDRO-3H-PYRROLO[1,2-a]PYRROLE-1-CARBOXYLIC ACID DERIVATIVES AND PROCESS FOR THE PRODUCTION THEREOF

[75] Inventors: Joseph M. Muchowski, Sunnyvale; Arthur F. Kluge, Los Altos, both of Calif.

[73] Assignee: Syntex (U.S.A.) Inc., Palo Alto, Calif.

[21] Appl. No.: 771,283

[22] Filed: Feb. 23, 1977

Related U.S. Application Data

[63] Continuation-in-part of Ser. No. 704,857, Jul. 14, 1976, abandoned.

[51] Int. Cl.² .................. C07D 209/00; A61K 31/40
[52] U.S. Cl. ........................ 424/274; 260/326.22; 260/326.25; 260/326.31; 260/326.46; 260/DIG. 8
[58] Field of Search .............. 260/326.25, 326.22; 424/274

[56] References Cited

PUBLICATIONS

Kochetkov et al., Chem. Abs., vol. 55: 1574a, (1961).
Adams et al., Chem. Abs., vol. 37: 6417, (1942).
Brandange et al., Chem. Abs., vol. 76: 25024t, (1972).
Carelli et al., Chem. Abs., vol. 59: 7463c, (1963).

*Primary Examiner*—Donald G. Daus
*Assistant Examiner*—Mary Vaughn
*Attorney, Agent, or Firm*—Gerard A. Blaufarb

[57] ABSTRACT

Novel 5-substituted-1,2-dihydro-3H-pyrrolo[1,2-a]pyrrole-1-carboxylic acid compounds represented by the formulas

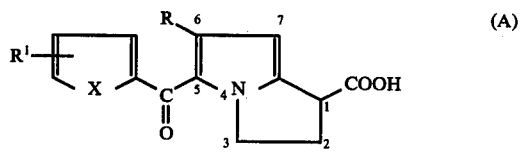

(A)

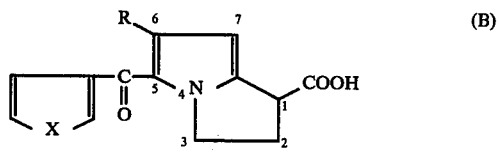

(B)

and the pharmaceutically acceptable, non-toxic esters and salts thereof, wherein X is oxygen or sulphur, R is hydrogen or a lower alkyl group having from 1 to 4 carbon atoms and $R^1$ is hydrogen, methyl, chloro or bromo, the $R^1$ substitution being at the 3, 4 or 5 positions of the furan or thiophene ring in the compounds of Formula (A), and process for the production thereof; 5-(2-thenoyl)-1,2-dihydro-3H-pyrrolo-[1,2-a]pyrrole-1-carboxylic acid and 5-(3-furoyl)-1,2-dihydro-3H-pyrrolo[1,2-a]pyrrole-1-carboxylic acid are representative of the class. These compounds, as the racemic mixture or the (1)-isomer, are useful as anti-inflammatory, analgesic and antipyretic agents and as smooth muscle relaxants.

39 Claims, No Drawings

5-(2-FUROYL)-, 5-(2-THENOYL)-, 5-(3-FUROYL)- AND 5-(3-THENOYL)-1,2-DIHYDRO-3H-PYRROLO[1,2-a]PYRROLE-1-CARBOXYLIC ACID DERIVATIVES AND PROCESS FOR THE PRODUCTION THEREOF

This application is a continuation-in-part of application Ser. No. 704,857, filed July 14, 1976, now abandoned.

The present invention relates to certain novel pyrrole-1-carboxylic acid compounds and to a process for the production thereof.

More particularly, this invention relates to novel 1,2-dihydro-3H-pyrrolo[1,2-a]pyrrole-1-carboxylic acids substituted at the C-5 position by a 2-furoyl, 2-thenoyl, 3-furoyl or 3-thenoyl group, represented by the formulas

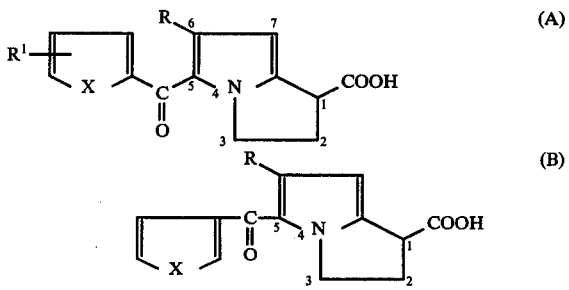

and the individual (l)-acid isomers and the (d)-acid isomers thereof and the pharmaceutically acceptable, non-toxic esters and salts thereof, wherein X is oxygen or sulphur; R is hydrogen or a lower alkyl group having from 1 to 4 carbon atoms and $R^1$ is hydrogen, methyl, chloro or bromo, the $R^1$ substitution in the compounds of Formula (A) being at the 3, 4 or 5 positions of the furan or thiophene ring, and to the method for the production thereof.

The compounds of the present invention as described above and more fully below, exclusive of the (d)-acid isomers and derivatives thereof, exhibit anti-inflammatory, analgesic and anti-pyretic activities and thus are useful in the treatment of inflammation, pain and/or pyrexia in mammals, as described hereinafter in detail. They are also smooth muscle relaxants.

The term "pharmaceutically acceptable, non-toxic esters and salts" as used herein refers to "alkyl esters" derived from hydrocarbons of branched or straight chain having from one to twelve carbon atoms and salts derived from pharmaceutically acceptable non-toxic inorganic and organic bases, respectively.

Typical alkyl ester groups are methyl, ethyl, propyl, isopropyl, butyl, t-butyl, isoamyl, pentyl, isopentyl, hexyl, octyl, nonyl, isodecyl, 6-methyldecyl and dodecyl esters.

Salts derived from inorganic bases include sodium, potassium, lithium, ammonium, calcium, magnesium, ferrous, zinc, copper, manganous, aluminum, ferric, manganic salts and the like. Particularly preferred are the ammonium, potassium, sodium, calcium and magnesium salts. Salts derived from pharmaceutically acceptable organic non-toxic bases include salts of primary, secondary, and tertiary amines, substituted amines including naturally occuring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, tromethamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic non-toxic bases are isopropylamine, diethylamine, ethanolamine, piperidine, tromethamine, choline and caffeine.

The novel compounds of Formulas (A) and (B), and Formulas (XI) and (XII) depicted below exist as pairs of optical isomers (or enantiomorphs), i.e., a (dl) mixture. However, each optical isomer as well as the (dl) mixtures thereof are included within the present invention.

When the novel compounds of this invention are to be used to elicit a physiological response (e.g., anti-inflammatory, analgesic or anti-pyretic activity), i.e., they are to be used as medicinals, a preferred sub-grouping is that of the compounds of Formulas (A) and (B), and the (l)-acid isomers thereof and the esters and pharmaceutically acceptable salts thereof.

A still further sub-grouping, for compounds to be used as medicinals are the compounds of Formula (A) and the (l)-acid isomer of Formula (A) and the esters and pharmaceutically acceptable salts thereof, and this sub-grouping may be divided into two further sub-groupings made up of (a) the compound of Formula (A), i.e., the (dl)-compound wherein R and $R^1$ are both hydrogen and X is sulfur and (b) the (l)-acid isomer of Formula (B) wherein R and $R^1$ are both hydrogen and X is sulfur and the esters and pharmaceutically acceptable salts thereof.

The (d)-acid isomer of Formulas (A) and (B) and the esters and pharmaceutically acceptable salts thereof are useful as intermediates for the preparation of the (dl)-acid of Formulas (A) and (B), as described more fully below.

The novel (dl) compounds of the present invention can be prepared by a process illustrated by the following reaction sequence:

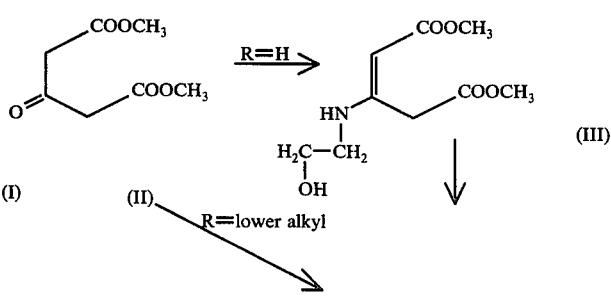

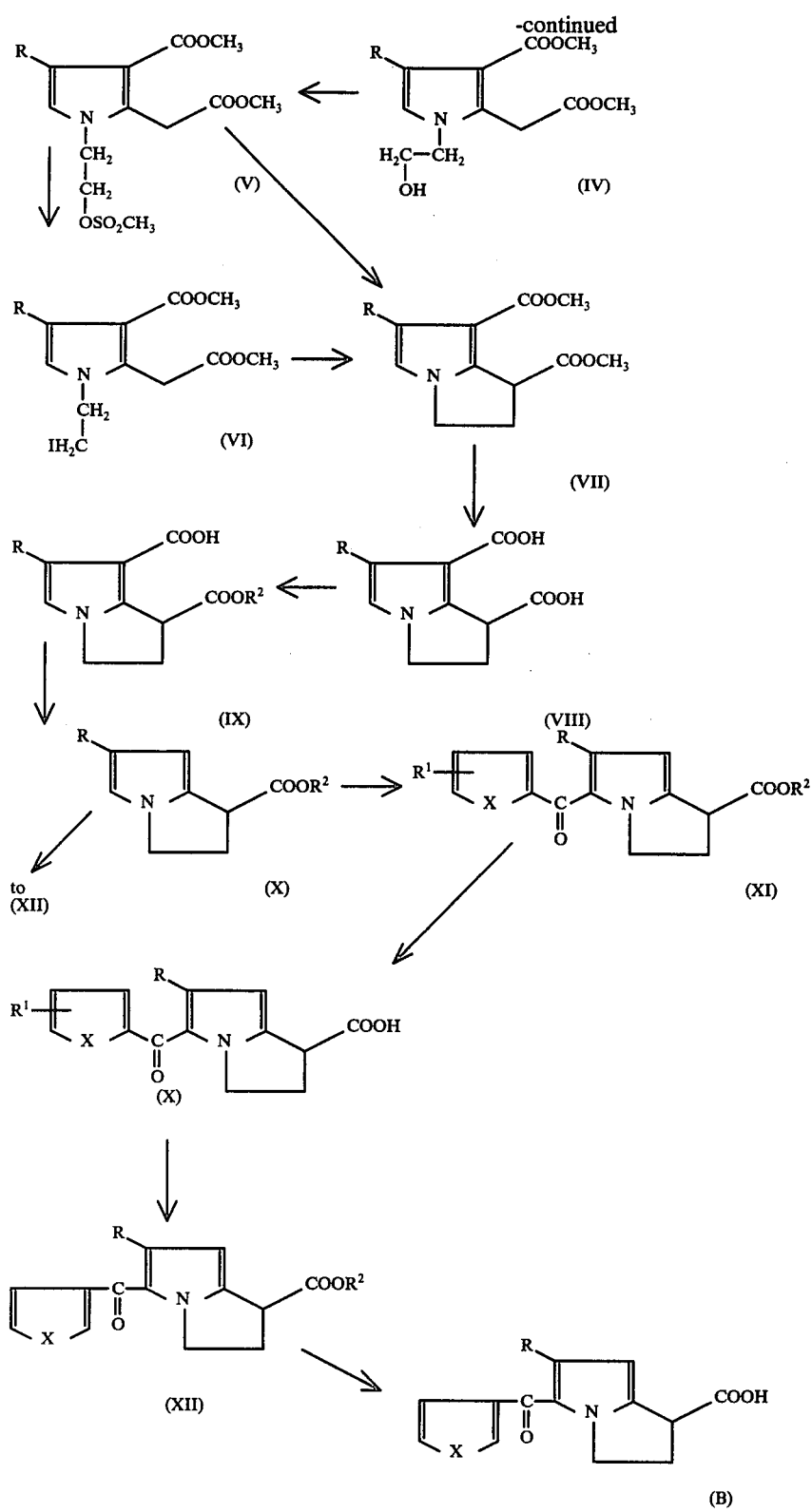

wherein X, R and R[1] have the above-indicated meaning and R[2] is a lower alkyl group of 1 to 4 carbon atoms, e.g., methyl, ethyl, isopropyl or n-butyl.

In practicing the process outlined above, for the preparation of the compound of Formula (IV) wherein R is hydrogen, equimolecular amounts of ethanolamine (I) and dimethyl 1,3-acetonedicarboxylate (II) are reacted at a temperature of from about 0° to about room temperature, to readily form a solution of the vinylamine of Formula (III), which is then treated, preferably in situ, in a suitable inert organic solvent, under anhydrous conditions, with 2-bromoacetaldehyde or 2-chloroacetaldehyde, at from about 40° to about 100° C for a period of time of from about 30 minutes to about 16 hours. Suitable solvents for this reaction are the aprotic solvents such as acetonitrile, tetrahydrofuran, dimethoxyethane, chloroform, dichloromethane and the like. In the preferred embodiments, the reaction is conducted in acetonitrile solution, at reflux temperature for about 1 hour. The 2-bromo-(chloro)-acetaldehyde reagents are known compounds, or can be obtained by pyrolysis of the corresponding diethyl acetals in the presence of oxalic acid dihydrate.

To prepare the compounds of Formula (IV) wherein R is a lower alkyl group, preferably straight chain, having 1 to 4 carbon atoms, an aqueous mixture of ethanolamine (I) and dimethyl 1,3-acetonedicarboxylate (II) is treated with a compound of the formula

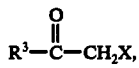

wherein X is bromo or chloro and $R^3$ is a lower alkyl group, preferably straight chain, of from 1 to 4 carbon atoms, and most preferably 1-bromoacetone, 1-bromo-2-butanone, 1-bromo-2-pentanone, and 1-bromo-2-hexanone, at from about 40° to about 100° C for a period of time from about 30 minutes to about 16 hours. In the preferred embodiment the reaction is conducted at a temperature of from about −10° C to about room temperature for from about 1 hour to about 6 hours. The

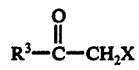

reagents are known compounds.

Esterification of compound (IV) with methanesulfonyl chloride in the presence of a tertiary amine, i.e., triethylamine, pyridine and the like, optionally in the presence of a cosolvent such as dichloromethane, at a temperature of from about −10° C to about room temperature, for about 10 minutes to about 2 hours produces the corresponding mesylate of Formula (V), which is converted into the corresponding N-(2-iodoethyl)pyrrole of Formula (VI) by reaction with sodium iodide in acetonitrile solution, at reflux temperature for from about 1 to about 10 hours.

Upon reaction of the iodoethyl compounds of Formula (VI) with sodium hydride in a suitable inert organic solvent such as dimethylformamide there are obtained dimethyl-1,2-dihydro-3H-pyrrolo[1,2-a]pyrrole-1,7-dicarboxylate and the 6-alkyl substituted derivatives thereof (VII). This cyclization is conducted under an inert atmosphere, i.e., under argon or nitrogen atmosphere, at temperatures of the order of from about 15° to about 40° C, for a period of time of from about 15 minutes to about 4 hours. Best results are obtained conducting the reaction at room temperature, for about 30 minutes when R is hydrogen.

Alternatively, the compounds of Formula (VII) can be prepared by direct cyclization of the mesylate (V), with sodium hydride in dimethylformamide solution, at from about −10° C to about room temperature, for from about 30 minutes to about 2 hours.

Basic hydrolysis of a compound of Formula (VII) with an alkali metal hydroxide or alkali metal carbonate, e.g., sodium hydroxide, potassium hydroxide, sodium carbonate, potassium carbonate and the like in an aqueous lower aliphatic alcohol, e.g., methanol or ethanol, at a temperature of between room temperature and reflux, for from about 4 to about 24 hours, affords the corresponding free diacid of Formula (VIII), i.e., 1,2-dihydro-3H-pyrrolo[1,2-a]pyrrole-1,7-dicarboxylic acid and the 6-alkyl derivatives thereof. The hydrolysis is preferably carried out using aqueous methanolic potassium hydroxide, at reflux temperature for about 10 hours.

The carboxylic acid group at the C-1 position in compound (VIII) is then selectively esterified by treatment with a lower aliphatic alcohol, e.g., methanol, ethanol, isopropanol, n-butanol and the like in the presence of hydrogen chloride, to produce the corresponding alkyl 1,2-dihydro-3H-pyrrolo[1,2-a]pyrrole-1-carboxylate-7-carboxylic acid of Formula (IX). The reaction is conducted at a temperature of from about 0° to about 50° C., for about 1 to about 4 hours.

Decarboxylation of the monoesterified compounds (IX) to the corresponding compounds of Formula (X), the key intermediates in the process for obtaining the compounds of the present invention, is achieved by heating (IX) at an elevated temperature, of the order of from about 230° to about 280° C, for a period of time sufficient to complete the reaction. The course of the reaction can be followed by the rate of carbon dioxide evolution and t.l.c. analysis, decarboxylation being generally completed within from about 45 to about 90 minutes. The reaction product, namely, alkyl 1,2-dihydro-3H-pyrrolo[1,2-a]pyrrole-1-carboxylate and the 6-alkyl derivatives thereof (X) can be purified by chromatographic techniques. Alternatively, and particularly for the decarboxylation of small batches of compound (IX), the reaction product (X) can be distilled directly from the reaction vessel.

Condensation of a compound (X) with an amide of the formulas

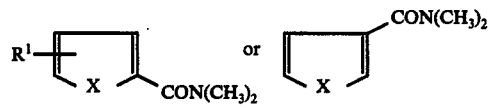

wherein X and $R^1$ have the above indicated meaning, affords the corresponding alkyl 5-substituted-1,2-dihydro-3H-pyrrolo[1,2-a]pyrrole-1-carboxylates of Formulas (XI) or (XII) respectively.

This reaction is conducted in an inert organic aprotic solvent and in the presence of phosphorous oxychloride, at reflux temperature for from about 1 to about 72 hours, under an inert atmosphere, followed by further reflux in the presence of sodium acetate, for from about 2 to about 10 hours. Alternatively, instead of phosphorous oxychloride other acid chlorides such as phosgene or oxalyl chloride may be used.

In the preferred embodiments, this condensation is carried out by adding a solution of compound (X) in a suitable solvent to a previously refluxed mixture of 1.1 to 2 molar equivalents of both the desired amide and phosphorous oxychloride in the same solvent, refluxing the reaction mixture thus obtained for from about 2 to about 30 hours under an argon atmosphere and thereafter adding thereto from about 3 to about 10 molar equivalents of sodium acetate, followed by an additional reflux period for from about 4 to about 6 hours.

Adequate solvents for this reaction are the halogenated hydrocarbons such as dichloromethane, 1,2-dichloroethane, chloroform, carbon tetrachloride and the like, dimethoxyethane and tetrahydrofuran. The preferred solvent is 1,2-dichloroethane.

Representative of the N,N-dimethyl amides which can be used are: N,N-dimethylthiophene-2-carboxamide, N,N-dimethylfuran-2-carboxamide,
N,N-dimethyl-3-methylthiophene-2-carboxamide,
N,N-dimethyl-4-methylthiophene-2-carboxamide,
N,N-dimethyl-5-methylthiophene-2-carboxamide,
N,N-dimethyl-4-chlorothiophene-2-carboxamide,
N,N-dimethyl-5-chlorothiophene-2-carboxamide,
N,N-dimethyl-3-bromothiophene-2-carboxamide,
N,N-dimethyl-5-bromothiophene-2-carboxamide,
N,N-dimethyl-3-methylfuran-2-carboxamide,
N,N-dimethyl-4-methylfuran-2-carboxamide,
N,N-dimethyl-4-chlorofuran-2-carboxamide,
N,N-dimethyl-5-chlorofuran-2-carboxamide,
N,N-dimethyl-4-bromofuran-2-carboxamide,
N,N-dimethyl-5-bromofuran-2-carboxamide,
N,N-dimethylthiophene-3-carboxamide and
N,N-dimethylfuran-3-carboxamide.

These amides can be prepared in a conventional manner from the corresponding thiophene- or furan-2-(3-carboxylic acids i.e., by conversion into the acid chlorides followed by treatment with dimethylamine.

Upon alkaline hydrolysis of the alkyl ester group in a compound of Formulas (XI) or (XII) there are obtained the corresponding free acids of Formulas (A) or (B), respectively. The hydrolysis is effected in a conventional manner, with an alkali metal hydroxide or alkali metal carbonate, e.g., sodium hydroxide, potassium hydroxide, sodium carbonate, potassium carbonate and the like, in an aqueous lower aliphatic alcohol, e.g., methanol, ethanol and the like, at a temperature of from about room temperature to reflux, for from about 30 minutes to about 4 hours, under an inert atmosphere. In the preferred embodiments, this hydrolysis is effected with aqueous methanolic potassium hydroxide, at reflux temperature for about 2 hours.

The compounds of Formulas (A) and (B) can be resolved, according to methods known in the art, to obtain the corresponding individual isomers thereof. Thus, for example, the compound of Formula (A) wherein R and R¹ are both hydrogen and X is sulfur can be subjected to further treatment in accordance with the following flow diagram:

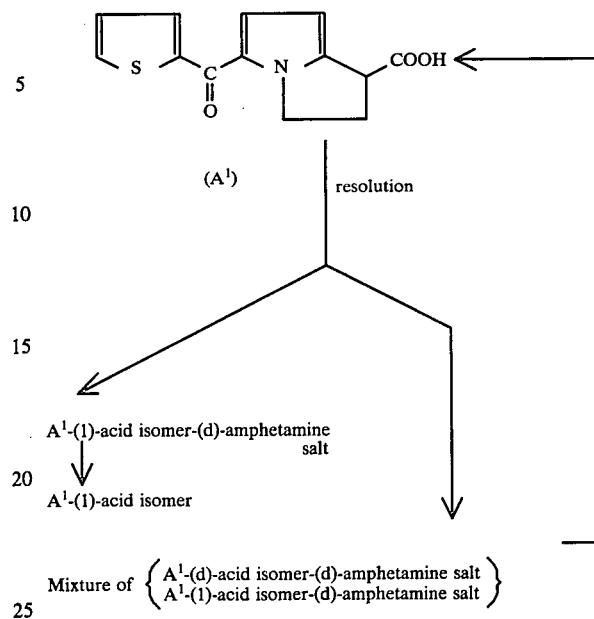

A more detailed description of this procedure is set forth in Example 10 B-1 below.

Alternatively, the (l)-acid isomers and (d)-acid isomers of the compounds of Formulas (A) and (B) can be obtained by applying the known technique of high pressure liquid chromotography (HPLC) to the α-phenethyl diastereoisomeric esters of the compounds of Formulas (A) and (B), followed by acid cleavage. Thus, for example, the compounds of Formula (A) wherein R and R¹ are both hydrogen and X is sulfur can be subjected to further treatment in accordance with the following flow diagram:

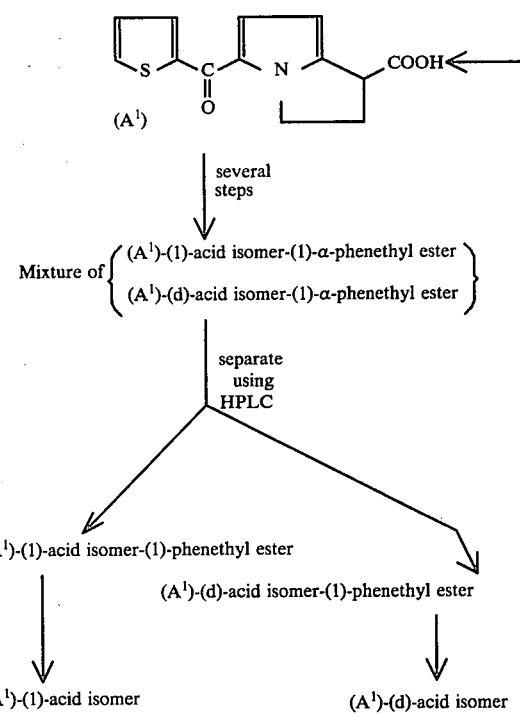

A more detailed description of this procedure is set forth in Example 10 B-2 below.

The free acids of Formulas (A) and (B) can be converted into other alkyl esters having from 1 to 12 carbon atoms by conventional methods, e.g., by treatment with (a) the alcohol corresponding to the desired ester in the presence of a strong mineral acid, (b) an etheral diazoalkane or (c) the desired alkyl iodide in the presence of lithium carbonate. The (l)-acid isomers can be converted into their alkyl esters by the methods of (b) and (c) above.

The salt derivatives of the compounds of Formulas (A) and (B) and the (l)-acid isomers thereof are prepared by treating these free acids with an appropriate amount of a pharmaceutically acceptable base. Representative pharmaceutically acceptable bases are sodium hydroxide, potassium hydroxide, lithium hydroxide, ammonium hydroxide, calcium hydroxide, magnesium hydroxide, ferrous hydroxide, zinc hydroxide, copper hydroxide, manganous hydroxide, aluminum hydroxide, ferric hydroxide, manganic hydroxide, isopropylamine, trimethylamine, diethylamine, triethylamine, tripropylamine, ethanolamine, 2-dimethylaminoethanol, 2-diethylaminoethanol, tromethamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. The reaction is conducted in water, alone or in combination with an inert, water-misible organic solvent, at a temperature of from about 0° to about 100° C, preferably at room temperature. Typical inert, water-miscible organic solvents include methanol, ethanol, isopropanol, butanol, acetone, dioxane or tetrahydrofuran. The molar ratio of compounds of Formulas (A) or (B) or the (l)-acid isomers thereof to base used are chosen to provide the ratio desired for any particular salt. For preparing, for example, the calcium salts or magnesium salts of the compounds of Formulas (A) or (B) or the (l)-acid isomers thereof, the free acid starting material can be treated with at least one-half molar equivalent of pharmaceutically acceptable base to yield a neutral salt. When the aluminum salts of the compounds of Formulas (A) or (B) or the (l)-acid isomers thereof are prepared at least one-third molar equivalent of the pharmaceutically acceptable base are employed if a neutral salt product is desired.

In the preferred procedure, the calcium salts and magnesium salts of the compounds of Formulas (A) and (B) and (l)-acid isomers thereof can be prepared by treating the corresponding sodium or potassium salts thereof with at least one-half molar equivalent of calcium chloride or magnesium chloride, respectively, in an aqueous solution, alone or in combination with an inert water-miscible organic solvent, at a temperature of from about 20° to about 100° C. Preferably, the aluminum salts of the compounds hereof, can be prepared by treating the corresponding free acids with at least one-third molar equivalent of an aluminum alkoxide, such as aluminum triethoxide, aluminum tripropoxide and the like, in a hydrocarbon solvent, such as benzene, xylene, cyclohexane and the like, at a temperature of from about 20° to about 115° C. Similar procedures can be used to prepare salts of inorganic bases which are not sufficiently soluble for easy reaction.

It is to be understood that isolation of the compounds described herein can be effected, if desired, by any suitable separation or purification procedure, such as, for example, extraction, filtration, evaporation, distillation, crystallization, thin-layer chromatography or column chromatography, high pressure liquid chromotography (HPLC) or a combination of these procedures. Illustrations of suitable separation and isolation procedures can be had by reference to the Examples herein below. However, other equivalent separation or isolation procedures could, of course, also be used.

While the (d)-acid isomers are not used as medicinal agents per se, they can, if desired, be converted to their pharmaceutically acceptable, non-toxic esters and salts thereof according to the methods described for the conversion of the (l)-acid isomers to their pharmaceutically acceptable, non-toxic esters and salts thereof.

The compounds of Formulas (A) and (B) and the (l)-acid isomers thereof and the pharmaceutically acceptable non-toxic esters and salts thereof, are useful as anti-inflammatory agents, analgetic agents, platelet aggregation inhibitors, fibrinolytic agents, and as smooth muscle relaxants. These compounds can be used both prophylactically and therapeutically.

The compositions containing these compounds are thus useful in the treatment and elimination of inflammation such as inflammatory conditions of the muscular skeletal system, skeletal joints and other tissues, for example, in the treatment of inflammatory conditions such as rheumatism, concussion, laceration, arthritis, bone fractures, post-traumatic conditions, and gout. In those cases in which the above conditions include pain and pyrexia coupled with inflammation, the instant compounds are useful for the relief of these conditions as well as the inflammation.

Administration of the active compounds of Formulas (A) or (B) or the (l)-acid isomers thereof and the pharmaceutically acceptable, non-toxic esters and salts thereof, in an appropriate pharmaceutical composition can be via any of the accepted modes of administration of agents for the treatment of inflammation, pain or pyrexia, or the prophylaxis thereof. Thus, administration can be for example, orally, parenterally or topically, in the form of solid, semi-solid or liquid dosage forms, such as, for example, tablets, suppositories, pills, capsules, powders, solutions, suspensions, emulsions, creams, lotions, ointments or the like, preferably in unit dosage forms suitable for simple administration of precise dosages. The compositions will include a conventional pharmaceutical carrier or excipient and an active compound of Formulas (A) or (B) or the (l)-acid isomers thereof and the pharmaceutically acceptable non-toxic esters and salts thereof, and, in addition, may include other medicinal agents, pharmaceutical agents, carriers, adjuvants, etc.

The preferred manner of administration, for the conditions detailed above, is oral using a convenient daily dosage regimen which can be adjusted according to the degree of affliction. Generally, a daily dose of from 25 mg. to 500 mg. of the active compound of Formulas (A) or (B) or the (l)-acid isomers thereof and the pharmaceutically acceptable, non-toxic esters and salts thereof is used. Most conditions respond to treatment comprising a dosage level of the order of 0.5 mg. to 6 mg. per kilogram of body weight per day. For such oral administration, a pharmaceutically acceptable, non-toxic composition is formed by the incorporation of any of the normally employed excipients, such as, for example, pharmaceutical grades of mannitol, lactose, starch, magnesium, stearate, sodium saccarine, talcum, cellulose, glucose, gelatin, sucrose, magnesium carbonate, and the like. Such compositions take the form of solutions, suspensions, tablets, pills, capsules, powders, sustained release formulations and the like.

The active compounds of Formulas (A) or (B) or the (l)-acid isomers thereof and the pharmaceutically acceptable, non-toxic esters and salts thereof, may be formulated into a suppository using, for example, polyalkylene glycols, for example, polypropylene glycol, as the carrier. Liquid pharmaceutically administerable compositions can, for example, be prepared by dissolving, dispersing, etc. an active compound, as described above, and optional pharmaceutical adjuvants in a carrier, such as, for example, water, saline, aqueous dextrose, glycerol, ethanol and the like, to thereby form a solution or suspension. If desired, the pharmaceutical composition to be administered may also contain minor amounts of non-toxic auxiliary substances such as wetting or emulsifying agents, pH buffering agents and the like, such as for example, sodium acetate, sorbitan monolaurate, triethanolamine oleate, etc.

Actual methods of preparing such dosage forms are known, or will be apparent, to those skilled in this art; for example, see Remington's Pharmaceutical Sciences, Mack Publishing Company, Easton, Pennsylvania, 14th. Edition, 1970. The composition to be administered will, in any event, contain a quantity of the active compound(s) in a pharmaceutically effective amount for relief of the particular condition being treated in accordance with the teachings of this invention.

The compounds of Formulas (A) and (B) and the (l)-acid isomers thereof and the non-toxic, pharmaceutically acceptable esters and salts thereof, described above, are also uterine smooth muscle relaxants and thus are useful as agents for maintaining the pregnancy of pregnant mammals, for the benefit of the mother and/or fetus, until termination of the pregnancy is considered, from a medical point of view, to be favorable, or more favorable, for the mother and/or the fetus. It should be understood, however, that in certain instances, for example where parturition has already begun (i.e., the mother is experiencing uterine contractions, especially near full term), that administration of the compounds herein described may not maintain the pregnant state for an indefinite period of time. Rather, in such instances, the pregnancy will, most probably, be slightly "prolonged", a factor which may be advantageous to either the mother and/or the fetus.

In particular, the compounds of Formulas (A) and (B) and the (l)-acid isomers thereof and the pharmaceutically acceptable, non-toxic esters and salts thereof, are used as agents for delaying the onset of, or for postponing, parturition. As used in this application, the phrase "to delay the onset of parturition" is intended to cover that delay in parturition caused by the administration of the compounds of Formulas (A) or (B) or the (l)-acid isomers thereof and the pharmaceutically acceptable, non-toxic esters and salts thereof, at any time before uterine muscle contractions have begun. Thus, it is intended that the aforementioned phrase cover abortion prevention early in pregnancy (i.e., before the fetus is "viable") as well as delaying premature parturition, a term which sometimes is used with reference to that premature labor experienced later in the pregnancy when the fetus is considered to be "viable". In either case, the agents are administered as prophylactic agents in that such administration tends to prevent the onset of parturition. This administration is particularly useful in the treatment of women having a history of spontaneous abortion, miscarriage or premature delivery (i.e., delivery prior to full term). Such administration is also useful where there are clinical indications that the pregnancy might be terminated prior to that time and is considered favorable to the mother and/or fetus.

With respect to animals, this treatment can also be utilized to synchronize the deliveries from a group of pregnant animals to happen at or about the same time, or to happen at or about a desired time and/or place, when the births can be handled with greater facility.

As used in this application, the phrase "postponing parturition" is intended to cover that delay in parturition caused by the administration of the compounds of Formulas (A) or (B) or the (l)-acid isomers thereof and the pharmaceutically acceptable, non-toxic esters and salts thereof after uterine muscle contractions have begun. The condition of the patient, including the time within the gestation period when the contractions have begun, the severity of the contractions and how long the contractions have taken place will affect the results achieved with the administration of the compounds hereof. For Example, the effect can be to reduce the intensity and/or the duration of the contractions (the actual act of parturition being "prolonged"), or to stop the contractions altogether. In either case, the effect will be to prolong the gestation period although, depending upon the conditions of the patient as described above, the effect may either be slight or, under appropriate circumstances, somewhat greater. Such administration may be to prevent spontaneous abortion, to cause the delivery to be more easily accomplished and/or less painful to the mother, or to occur at a more appropriate time and/or place.

In all cases, administration of the compounds of Formulas (A) or (B) or the (l)-acid isomers thereof and the pharmaceutically acceptable, non-toxic esters and salts thereof, for the purposes set forth herein should be consistent with best and/or accepted medical (or veterinary) practices so as to maximize the benefits to the mother and the fetus. For example, administration should not be continued so long past full term that the fetus dies in utero.

In the practice of the methods of the present invention, a therapeutically effective amount of a compound of Formulas (A) or (B) or the (l)-acid isomers thereof and the pharmaceutically acceptable, non-toxic esters and salts thereof, or a pharmaceutical composition containing same, is administered to the pregnant mammal via any of the usual and acceptable methods known in the art. The compound can be administered either singly or in combination with another compound or compounds, as defined above, or other pharmaceutical agents, carriers, adjuvants, etc. Such compound(s) or compositions can be administered orally, parenterally, either in the form of solid, semi-solid, or liquid dosage forms. Typically, administration is by a pharmaceutical composition containing the pharmaceutically active compound and one or more pharmaceutical carriers or adjuvants.

The administerable pharmaceutical composition may take the form of oral tablets, vaginal or uterine tablets or suppositories, pills, capsules, liquid solutions, suspensions, or the like, preferably in unit dosage forms suitable for simple administration of precise dosages. Conventional non-toxic solid carriers include, for example, pharmaceutical grades of mannitol, lactose, starch, magnesium stearate, sodium saccharin, talcum, cellulose, glucose, gelatin, sucrose, magnesium carbonate, and the like. The active compound as defined above may be formulated as suppositories using, for example, polyalkylene glycols, for example, polypropylene glycol, as the carrier. Liquid pharmaceutically administerable compositions can, for example, be prepared by dissolving, dispersing, etc. an active compound as defined above and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amounts of non-toxic auxiliary substances such as wetting or emulsifying agents, pH buffering agents and the like, for example, sodium acetate, sorbitan monolaurate, triethanolamine oleate, etc. Actual methods of preparing such dosage forms are known, or will be apparent, to those skilled in this art; for example, see Remington's Pharmaceutical Sciences, Mack Publishing Company, Easton, Pennsylvania, 14th Edition, 1970. The composition or formulation to be administered will, in any event, contain a quantity of the active compound(s) in an amount effective to delay the onset of parturition or to postpone parturition if uterine contractions have already begun. Generally a daily dose of from 0.5 mg. to about 25 mg. of the active compound per kilogram of body weight will be administered, with administration being a single daily dose or up to three or four smaller dosages regularly given throughout the day. The amount of active compound administered will, of course, depend on its relative activity.

The following Preparation and Examples illustrate the invention but are not intended to limit its scope. The abbreviation t.l.c. refers to thin-layer chromatography and all mixture ratios used with regard to liquids refer to volume ratios. Also where necessary, examples are repeated to prepare additional material for subsequent examples; and unless otherwise specified the reactions are carried out at room temperature (20° to 30° C).

PREPARATION

A mixture of 23 g. of 4-chlorothiophene-2-carboxylic acid (J. Iriarte et al., J. Heterocyclic Chem. 13, 393) and 80 ml. of thionyl chloride is heated to reflux, under anhydrous conditions for 4 hours. The excess thionyl chloride is eliminated and the residue distilled under reduced pressure (60° C/2 mm), to afford 18 g. of 4-chlorothiophene-2-carboxylic acid chloride.

A solution of 10.5 g. of 4-chlorothiophene-2-carboxylic acid chloride in 500 ml. of anhydrous benzene is cooled in an ice water bath and dimethylamine is slowly bubbled through the solution for 30 minutes. The ice water bath is removed, maintaining the stream of dimethylamine for 15 additional minutes. The reaction mixture is then diluted with 100 ml. of 10% sodium chloride solution and stirred for 5 minutes at room temperature, the organic phase is separated, washed with 10% hydrochloric acid, saturated sodium bicarbonate solution and saturated sodium chloride solution, dried over sodium sulfate and evaporated to dryness under reduced pressure, to produce N,N-dimethyl-4-chlorothiophene-2-carboxamide.

In a similar manner the thiophene and furan-2-carboxylic acids listed below under I are converted into the N,N-dimethyl amides listed under II:

| I | II |
|---|---|
| Thiophene-2-carboxylic acid | N,N-dimethylthiophene-2-carboxamide |
| furan-2-carboxylic acid | N,N-dimethylfuran-2-carboxamide |
| 3-methylthiophene-2-carboxylic acid | N,N-dimethyl-3-methylthiophene-2-carboxamide |
| 4-methylthiophene-2-carboxylic acid | N,N-dimethyl-4-methylthiophene-2-carboxamide |
| 5-methylthiophene-2-carboxylic acid | N,N-dimethyl-5-methylthiophene-2-carboxamide |
| 5-chlorothiophene-2-carboxylic acid | N,N-dimethyl-5-chlorothiophene-2-carboxamide |
| 3-bromothiophene-2-carboxylic acid | N,N-dimethyl-3-bromothiophene-2-carboxamide |
| 4-bromothiophene-2-carboxylic acid | N,N-dimethyl-4-bromothiophene-2-carboxamide |
| 5-bromothiophene-2-carboxylic acid | N,N-dimethyl-5-bromothiophene-2-carboxamide |
| 3-methylfuran-2-carboxylic acid | N,N-dimethyl-3-methylfuran-2-carboxamide |
| 4-methylfuran-2-carboxylic acid | N,N-dimethyl-4-methylfuran-2-carboxamide |
| 5-methylfuran-2-carboxylic acid | N,N-dimethyl-5-methylfuran-2-carboxamide |
| 3-chlorofuran-2-carboxylic acid | N,N-dimethyl-3-chlorofuran-2-carboxamide |
| 4-chlorofuran-2-carboxylic acid | N,N-dimethyl-4-chlorofuran-2-carboxamide |
| 5-chlorofuran-2-carboxylic acid | N,N-dimethyl-5-chlorofuran-2-carboxamide |
| 4-bromofuran-2-carboxylic acid | N,N-dimethyl-4-bromofuran-2-carboxamide |
| 5-bromofuran-2-carboxylic acid | N,N-dimethyl-5-bromofuran-2-carboxamide |
| thiophene-3-carboxylic acid | N,N-dimethylthiophene-3-carboxamide |
| furan-3-carboxylic acid | N,N-dimethylfuran-3-carboxamide |

EXAMPLE 1

A 250 ml. 3-necked round bottomed flask containing a magnetic stirring bar and fitted with a calcium chloride filled drying tube is connected directly (via one of the outer necks) by means of a receiver adapter and short (3-inch) water condenser to the acetal pyrolysis apparatus. This latter apparatus consists of a 100 ml. round bottom flask [previously charged with 15.6 g. of oxalic acid dihydrate and 11.82 g. of bromoacetaldehyde diethyl acetal, prepared from vinyl acetate, as described by P. Z. Bedoukian, J. Am. Chem. Soc. 66, 651 (1944)], topped with a 6-inch Vigreux column, bearing a thermometer, connected to the above mentioned condenser.

The 3-necked flask is charged with 3.36 g. of ethanolamine cooled in an ice bath at 0°–10° C and treated dropwise, with stirring, with 8.7 g. of dimethyl 1,3-acetonedicarboxylate. Methyl 3-carbomethoxymethyl-3(2'-hydroxyethyl)amino acrylate (III) forms immediately. When the addition is completed, the ice bath is removed and 100 ml. of dry acetonitrile is added. The pyrolysis part of the apparatus is placed in an oil bath and the temperature thereof is raised to 150°–160° C. The bromoacetaldehyde solution which forms is distilled (b.p. 80°–83° C/580 mm) directly into the magnetically stirred solution of the vinylamine (III). When the distillation temperature drops below 80° C, the pyrolysis apparatus is disconnected and replaced by a reflux condenser fitted with a drying tube containing calcium chloride. The solution is heated at reflux temperature for 1 hour, the solvent is removed under reduced pressure and then 200 ml. of methanol and 20 g. of silica gel are added to the residue. This mixture is evaporated to dryness in vacuum and placed on top of a column of 200 g. of silica gel packed in hexane. The column is then eluted with hexane:ethyl acetate (80:20; 500 ml.) and hexane:ethyl acetate (1:1, 9 × 500 ml.). Fractions 2 and 3 contain less polar impurities and dimethyl 1,3-acetonedicarboxylate; fractions 4–8 afford 4.1 g. of methyl N-(2-hydroxyethyl)-3-carbomethoxypyrrole-2-acetate (IV, R=H), which upon recrystallization from ether-hexane has a melting point of 52°–54° C.

EXAMPLE 2

To a stirred solution of 4.1 g. of methyl N-(2-hydroxyethyl)-3-carbomethoxypyrrole-2-acetate in 35 ml. of dry dichloromethane cooled to −10° C, are added 2.65 ml. of triethylamine and thereafter, in a dropwise fashion, 1.46 ml. of methanesulfonyl chloride, maintaining the temperature of the reaction mixture at −10° to −5° C. The course of the reaction is followed by t.l.c. analysis using chloroform:acetone (90:10). When the reaction appears to be complete (about 30 minutes after the addition of the methanesulfonyl chloride is terminated) there is added slowly 10 ml. of water. The organic phase is separated, washed with water (3 × 30 ml.), dried over sodium sulfate and evaporated under reduced pressure. Crystallization of the residue from dichloromethane-hexane affords 4.75 g. (77.7%) of methyl N-(2-mesyloxyethyl)-3-carbomethoxypyrrole-2-acetate (V, R = H), m.p. 99°–101° C.

EXAMPLE 3

A solution of 785 mg. of methyl N-(2-mesyloxyethyl)-3-carbomethoxypyrrole-2-acetate and 1.83 g. of sodium iodide in 10 ml. of acetonitrile is refluxed for 1 hour. The cooled reaction mixture is evaporated to dryness under reduced pressure and the residue is triturated with water. The insoluble material is separated by filtration and air dried, thus obtaining 840 mg. (97%) of methyl N-(2-iodoethyl)-3-carbomethoxypyrrole-2-acetate (VI, R = H), m.p. 137°–138° C.

EXAMPLE 4

A solution of 1 g. of methyl N-(2-iodoethyl)-3-carbomethoxypyrrole-2-acetate in 5 ml. of dry dimethylformamide is stirred, under an atmosphere of argon, with 137 mg. of 50% sodium hydride in mineral oil. The reaction mixture is maintained for 30 minutes at room temperature and then quenched with 100 ml. of water. The product is extracted with ethyl acetate (3 × 50 ml.), the combined extracts are washed with water, dried over magnesium sulfate and evaporated to dryness. Chromatography of the residue on silica gel (20 g.) using hexane:ethyl acetate (4:1) as eluant affords 500 mg. (80%) of dimethyl 1,2-dihydro-3H-pyrrolo [1,2-a]pyrrole-1,7-dicarboxylate (VII, R = H) m.p. 70°–71° C.

A solution of 1.80 g. of dimethyl 1,2-dihydro-3H-pyrrolo[1,2-a]pyrrole-1,7-dicarboxylate in 20 ml. of methanol is treated with a solution of 4.48 g. of potassium hydroxide in 20 ml. of water, and the reaction mixture is refluxed for 6 hours. The cooled solution is evaporated to dryness and the residue is treated with 50 ml. of saturated sodium chloride solution. The resultant solution is acidified with 6N hydrochloric acid and extracted with ethyl acetate (3 × 50 ml.). The combined extracts are dried over magnesium sulfate and evaporated to dryness under reduced pressure, to yield 1.51 g. (95%) of 1,2-dihydro-3H-pyrrolo[1,2-a]pyrrole-1,7-dicarboxylic acid (VIII, R = H), m.p. 220° C, with decomposition.

EXAMPLE 5

A solution of 1.34 g. of 1,2-dihydro-3H-pyrrolo[1,2-a]pyrrole-1,7-dicarboxylic acid in 50 ml. of isopropanol, cooled in an ice bath is saturated with gaseous hydrogen chloride, maintaining the temperature of the reaction mixture below 50° C. The ice bath is then removed and the reaction mixture is stirred for 1.5 hours at room temperature, and evaporated to dryness under reduced pressure; 10 ml. of benzene is added to the residue and the solution is evaporated under vacuum once again, repeating this process a total of three times to completely remove the excess hydrogen chloride, thus obtaining 1.58 g. (96%) of isopropyl 1,2-dihydro-3H-pyrrolo[1,2-a]pyrrole-1-carboxylate-7-carboxylic acid (IX, R = H, $R^2$ = $iC_3H_7$), which upon crystallization from methanol-ethyl acetate has a melting point of 144°–145° C.

In a similar manner but substituting methanol, ethanol, propanol, and n-butanol for isopropanol in the above procedure there are respectively obtained:

methyl 1,2-dihydro-3H-pyrrolo[1,2-a]pyrrole-1-carboxylate-7-carboxylic acid, ethyl 1,2-dihydro-3H-pyrrolo[1,2-a]pyrrole-1-carboxylate-7-carboxylic acid, propyl 1,2-dihydro-3H-pyrrolo[1,2a]pyrrole-1-carboxylate-7-carboxylic acid, and butyl 1,2-dihydro-3H-pyrrolo[1,2-a]pyrrole-1-carboxylate-7-carboxylic acid.

EXAMPLE 6

1.054 G. of isopropyl 1,2-dihydro-3H-pyrrolo[1,2-a]pyrrole-1-carboxylate-7-carboxylic acid is heated to 240°–250° C in a dry 10 ml. round bottomed flask, distilling directly the reaction product from the reaction vessel. In this manner there is obtained 745 mg. (87%) of isopropyl 1,2-dihydro-3H-pyrrolo[1,2-a]pyrrole-1-carboxylate (X, R = H, $R^2$ = $iC_3H_7$), a pale yellow oil, having the following physical constants: U.V.: $\lambda_{max}^{MeOH}$ 215 nm ($\epsilon$ 6020); I.R.: $\nu_{max}^{CHCl_3}$ 1725 cm$^{-1}$; N.M.R.: $\delta_{TMS}^{CDCl_3}$ 1.22 (d, J = 7 Hz, 6H), 2.40–2.90 (m, 2H), 3.60–4.20 (m, 2H), 4.65–5.2 (m, 1H), 5.73–5.92 (m, 1H), 6.10 (t, J = 3 Hz, 1H), 6.43–6.53 (m, 1H).

EXAMPLE 7

A 100 ml. 3-necked round bottomed flask equipped with a condenser, nitrogen inlet tube and a gas bubbler is charged with 5.0 g. of isopropyl 1,2-dihydro-3H-pyrrolo[1,2-a]pyrrole-1-carboxylate-7-carboxylic acid. The apparatus is thoroughly flushed with nitrogen and then the nitrogen flow is stopped. The apparatus is immersed in an oil bath heated at 270° C and the reaction is followed by the rate of carbon dioxide evolution (gas bubbler) and by t.l.c. on silica gel, using benzene:dioxan:acetic acid (90:10:1) as developing solvent. After 45 minutes the reaction is almost complete. After one hour, the vessel is removed from the oil bath and the contents of the reaction flask are transferred to a round bottomed flask with 500 ml. of acetone. The solvent is removed under reduced pressure, and the residue is purified by column chromatography on 100 g. of silica gel. The fractions eluted with hexane:benzene (70:30) and hexane:benzene (50:50) afford 2.77 g. (68%) of isopropyl 1,2-dihydro-3H-pyrrolo[1,2-a]pyrrole-1-carboxylate (X, R = H, $R^2$ = $iC_3H_7$), an oil, whose physical constants are identical to those obtained in Example 6.

EXAMPLE 8

710 Mg. of a 50% suspension of sodium hydride in mineral oil is washed with anhydrous hexane under an atmosphere of nitrogen, and then suspended in 50 ml. of dimethylformamide. The suspension is cooled to −5° C and 4.5 g. of methyl N-(2-mesyloxymethyl)-3-carbomethoxypyrrole-2-acetate are added, stirring the reaction mixture at −5° to 0° C for 1 hour. It is then poured into iced sodium chloride solution and extracted several times with benzene. The combined extracts are washed with water, dried and evaporated to dryness under reduced pressure. The solid residue is crystallized from ether, thus obtaining dimethyl 1,2-dihydro-3H-pyrrolo[1,2-a]pyrrole-1,7-dicarboxylate (VII, R = H) identical to the product obtained in Example 4.

EXAMPLE 9

A solution of 232.5 mg. of N,N-dimethylthiophene-2-carboxamide and 0.15 ml. of phosphorous oxychloride in 2 ml. of 1,2-dichloroethane is refluxed for 30 minutes. To this solution is added a solution of 181 mg. of isopropyl 1,2-dihydro-3H-pyrrolo[1,2-a]pyrrole-1-carboxylate in 2 ml. of 1,2-dichloroethane. The reaction mixture is refluxed under an argon atmosphere for 8 hours, treated with 450 mg. of sodium acetate and refluxed for a further 5 hours. The resultant mixture is then evaporated to dryness and the residue is chromatographed on 12 g. of silica gel, eluting with hexane:ethyl acetate (3:1), thus obtaining isopropyl 5-(2-thenoyl)-1,2-dihydro-3H-pyrrolo[1,2-a]pyrrole-1-carboxylate (XI, R and $R^1$ = H, $R^2$ = $iC_3H_7$, X = S).

EXAMPLE 10 A

A solution of 300 mg. of isopropyl 5-(2-thenoyl)-1,2-dihydro-3H-pyrrolo[1,2-a]pyrrole-1-carboxylate in 30 ml. of 50% aqueous methanol containing 1% of potassium hydroxide is refluxed under an atmosphere of nitrogen for 2 hours. The methanol is then removed under reduced pressure and the basic solution which remains is diluted with water and extracted with chloroform to remove any unsaponifiable product. The aqueous alkaline phase is acidified with 20% hydrochloric acid and extracted three times with ethyl acetate. The combined extracts are dried over sodium sulfate and evaporated to dryness under reduced pressure, thus obtaining 250 mg. of crude 5-(2-thenoyl)-1,2-dihydro-3H-pyrrolo-[1,2-a]pyrrole-1-carboxylic acid, [(A), R and $R^1$ = H, X = S], having a melting point of 145°–148° C, which upon recrystallization from ethyl acetate melts at 152°–153° C, with decomposition.

EXAMPLE 10 B-1

410 Mg. of 5-(2-thenoyl)-1,2-dihydro-3H-pyrrolo-[1,2-a]pyrrole-1-carboxylic acid and 212.3 mg. of (d)-amphetamine are dissolved in 15 ml. of absolute methanol and heated at reflux for 15 minutes, followed by removal of the methanol under vacuum. The resulting diastereoisomeric-(d)-amphetamine salt mixture (612.3 mg.) is dissolved in a minimum volume of hot (55° C) acetone, cooled to room temperature, filtered and washed with 2 ml. of cold (−10° C) acetone. This recrystallization procedure was repeated three additional times to yield 247 mg. of (l)-5-(2-thenoyl)-1,2-dihydro-3H-pyrrolo-[1,2-a]pyrrole-1-carboxylic acid-(d)-amphetamine salt having an $\alpha_D^{CHCl_3}$ −181.3° and a melting point of 168°–170° C.

The (l)-acid isomer-(d)-amphetamine salt, obtained immediately above, is added to 30 ml. of methylene chloride and shaken three times with 10 ml. of 0.1N aqueous hydrochloric acid. The methylene chloride solution is washed three times with 15 ml. of saturated sodium chloride/water (2:1/V:V) and dried over anhydrous sodium sulfate. Filtration and removal of the organic solvent under vacuum yields 90 mg. of (l)-5-2-(thenoyl)-1,2-dihydro-3H-pyrrolo-[1,2-a]pyrrole-1-carboxylic acid, which has an $\alpha_D^{CHCl_3}$ −177° and a melting point of 134°–135.5° C.

The acetone mother liquors resulting from the resolution (i.e., the multiple crystallizations) of the diastereoisomeric-(d)-amphetamine salt mixture, described above, are combined and converted, using the hydrochloric acid cleavage procedure as described above, to yield 245 mg. of a mixture enriched in (d)-5-(2-thenoyl)-1,2-dihydro-3H-pyrrolo-[1,2-a]pyrrole-1-carboxylic acid and containing (l)-5-(2-thenoyl)-1,2-dihydro-3H-pyrrolo-[1,2-a]pyrrole-1-carboxylic acid. This mixture is racemized (recycled) back to a 1:1 mixture of the (d)-and (l)-isomers of 5-(2-thenoyl)-1,2-dihydro-3H-pyrrolo-[1,2-a]pyrrole-1-carboxylic acid as follows: The 245 mg. of the mixture enriched in the (d)-isomer and containing the (l)-isomer, described above, is dissolved in 15 ml. of methanol. 1.5 Ml. of methanol and 350 mg. of sodium hydroxide are added and the solution is heated at reflux, under nitrogen, for 1 hour. The methanol is removed under vacuum, 2.5 ml. of water is added and the solution acidified to pH 2 with 10% aqueous hydrochloric acid. The mixture is extracted with three 10 ml. portions of methylene chloride and the methylene chloride extracts are combined and back-washed to neutrality (pH 7), dried over anhydrous sodium sulfate and concentrated in vacuo to yield 230 mg. of a crude crystalline product, which upon recrystallization from ethyl acetate-hexane yields 180 mg. of 5-(2-thenoyl)-1,2-dihydro-3H-pyrrolo-[1,2-a]pyrrole-1-carboxylic acid having an $\alpha_D^{MeOH}$ 0.0° and a melting point of 152°–154° C.

In like manner other (d)-optically active bases may be substituted for (d)-amphetamine in the above process. Particularly suitable are:
 (d)-p-bromo-α-phenethylamine,
 (d)-α-phenethylamine,
 (d)-α-1-naphthethylamine, and
 (d)-α-2-naphthethylamine,
with (d)-p-bromo-α-phenethylamine being most preferred after (d)-amphetamine.

Similarly, the (d)-acid isomers e.g., (d)-5-(2-thenoyl)-1,2-dihydro-3H-pyrrolo-[1,2-a]pyrrole-1-carboxylic acid, are obtained by substituting the (l)-optically active bases for the (d)-optically active bases, e.g., the substitution of (l)-amphetamine for (d)-amphetamine.

EXAMPLE 10 B-2

To a solution of 118 mg. of 5-(2-thenoyl)-1,2-dihydro-3H-pyrrolo[1,2-a]pyrrole-1-carboxylic acid in 8 ml. of dry benzene, 0.234 g. of trifluoroacetic anhydride is added. The mixture is stirred at room temperature for 10 minutes and the resulting solution is cooled to 0°–5° C and 0.55 g of dry triethylamine is added, followed immediately by the addition of 0.2 g of (l)-α-phenyl ethyl alcohol. The thus-obtained reaction solution is stirred at room temperature for 15 minutes and poured into 20 ml. of water containing 1 ml. of triethylamine, followed by extraction with ethyl acetate. The ethyl acetate extract is dried over sodium sulfate, followed by removal of the solvent and excess (l)-α-phenyl ethyl alcohol under vacuum to yield 0.166 g. of a mixture of (l)-5-(2-thenoyl)-1,2-dihydro-3H-pyrrolo-[1,2-a]pyrrole-1-carboxylic acid-(l)-α-phenethyl ester and (d)-5-(2-thenoyl)-1,2-dihydro-3H-pyrrolo[1,2-a]pyrrole-1-carboxylic acid-(l)-α-phenethyl ester which is separated by high pressure liquid chromatography (using 4% EtOAc/hexane on a 11 mm. × 50 cm., 10μm. Lichrosorb Sl-60 column) to give 68 mg. of a more polar ester ($\alpha_D^{MeOH}$ −149.1°) and 73 mg. of a less polar ester ($\alpha_D^{MeOH}$ +105.2°).

62.1 Mg. of the more polar ester is dissolved in 3 ml. of dry benzene. The solution is cooled to 15°–20° C and 2.5 ml. of trifluoroacetic acid is added and the solution stirred at room temperature for 1 hour and 40 minutes. The reaction solution is poured into 60 ml. of dry benzene and the solvents are removed under vacuum and at ambient temperature. Purification is effected by high pressure liquid chromatography (using a column as that described above, except that 35% EtOAc/hexane in ½% acetic acid is substituted for 4% EtOAc/hexane) to give 41 mg. (l)-5-(2-thenoyl)-1,2-dihydro-3H-pyrrolo-[1,2-a]pyrrole-1-carboxylic acid having an $\alpha_D^{MeOH}$ −144°, and a melting point of 130°–132° C.

Similarly, cleavage of the less polar ester, according to the method described above for the cleavage of the more polar ester, yields (d)-5-(2-thenoyl)-1,2-dihydro-3H-pyrrolo[1,2-a]pyrrole-1-carboxylic acid having an $\alpha_D^{MeOH}$ +142.4°, and a melting point of 127°–129° C. The thus-obtained (d)-acid isomer may, if desired, be racemized (and recycled), according to methods known in the art.

Similarly other (dl) compounds may be converted to their respective (l)-isomers and (d)-isomers.

EXAMPLE 11

A solution of 336 mg. of isopropyl 5-(2-thenoyl)-1,2-dihydro-3H-pyrrolo[1,2-a]pyrrole-1-carboxylate in 10 ml. of methanol is treated with a solution of 690 mg. of potassium carbonate in 5 ml. of water. The reaction mixture is refluxed under nitrogen atmosphere for 2 hours, cooled, and evaporated to dryness. The residue is taken up in 10 ml. of 10% aqueous hydrochloric acid and 50 ml. of water and the resultant mixture extracted with ethyl acetate (2 × 50 ml.). The combined extracts are dried over magnesium sulfate and evaporated to dryness under reduced pressure. Crystallization of the residue from ethyl acetate affords 5-(2-thenoyl)-1,2-dihydro-3H-pyrrolo[1,2-a]pyrrole-1-carboxylic acid, identical to the product obtained in Example 10 A.

EXAMPLE 12

By following the methods of Examples 6 or 7, the remaining compounds obtained in Example 5 are converted respectively into:
methyl 1,2-dihydro-3H-pyrrolo[1,2-a]pyrrole-1-carboxylate,
ethyl 1,2-dihydro-3H-pyrrolo[1,2-a]pyrrole-1-carboxylate,
propyl 1,2-dihydro-3H-pyrrolo[1,2-a]pyrrole-1-carboxylate and
butyl 1,2-dihydro-3H-pyrrolo[1,2-a]pyrrole-1-carboxylate.

Upon condensation of these compounds with N,N-dimethylthiophene-2-carboxamide, in accordance with the method of Example 9 there are respectively obtained:

methyl 5-(2-thenoyl)-1,2-dihydro-3H-pyrrolo[1,2-a]pyrrole-1-carboxylate,
ethyl 5-(2-thenoyl)-1,2-dihydro-3H-pyrrolo[1,2-a]pyrrole-1-carboxylate, $\lambda_{max}^{MeOH}$ 265, 328 nm (ε 7580, 17780),
propyl 5-(2-thenoyl)-1,2-dihydro-3H-pyrrolo[1,2-a]pyrrole-1-carboxylate and
butyl 5-(2-thenoyl)-1,2-dihydro-3H-pyrrolo[1,2-a]pyrrole-1-carboxylate.

EXAMPLE 13

Following the procedure of Example 9, using 1.1 to 2 molar equivalents of
N,N-dimethylfuran-2-carboxamide,
N,N-dimethyl-3-methylthiophene-2-carboxamide,
N,N-dimethyl-4-methylthiophene-2-carboxamide,
N,N-dimethyl-5-methylthiophene-2-carboxamide,
N,N-dimethyl-4-chlorothiophene-2-carboxamide,
N,N-dimethyl-5-chlorothiophene-2-carboxamide,
N,N-dimethyl-3-bromothiophene-2-carboxamide,
N,N-dimethyl-4-bromothiophene-2-carboxamide,
N,N-dimethyl-5-bromothiophene-2-carboxamide,
N,N-dimethyl-3-methylfuran-2-carboxamide,
N,N-dimethyl-4-methylfuran-2-carboxamide,
N,N-dimethyl-5-methylfuran-2-carboxamide,
N,N-dimethyl-3-chlorofuran-2-carboxamide,
N,N-dimethyl-4-chlorofuran-2-carboxamide,
N,N-dimethyl-5-chlorofuran-2-carboxamide,
N,N-dimethyl-4-bromofuran-2-carboxamide and
N,N-dimethyl-5-bromofuran-2-carboxamide,
in place of N,N-dimethylthiophene-2-carboxamide, and monitoring the course of the reaction by t.l.c., there are obtained respectively:
isopropyl 5-(2-furoyl)-1,2-dihydro-3H-pyrrolo[1,2-a]pyrrole-1-carboxylate, an oil, having the following physical constants:

| | MeOH |
|---|---|
| U.V. | λmax 275, 332.5 nm (ε 8900, 17800); |
| | CHCl$_3$ |
| I.R. | νmax 1735, 1685, 1605 cm$^{-1}$; |
| | CDCl$_3$ |
| N.M.R. | δTMS 1.23 [d, 6H, J = 6 Hz; (CH$_3$)$_2$CH], 2.60–3.00 (m, 2H), 3.90 (dd, 1H, J$_{AX}$ = 6 Hz; J$_{BY}$ = 7 Hz; H-1), 4.10–4.67 (m, 2H), 4.95 [sept., 1H, J = 6 Hz; (CH$_3$)$_2$CH], 6.00 (d, 1H, J = 4 Hz; H-7), 6.40 (m, 1H), 7.10 (m, 1H), 7.23 (d, 1H, J = 4 Hz; H-6), 7.43 ppm (m, 1H); |
| M.S. m/e | 287 (M$^+$), | isopropyl 5-(3-methyl-2-thenoyl)-1,2-dihydro-3H-pyrrolo[1,2-a]pyrrole-1-carboxylate,
isopropyl 5-(4-methyl-2-thenoyl)-1,2-dihydro-3H-pyrrolo[1,2-a]pyrrole-1-carboxylate,
isopropyl 5-(5-methyl-2-thenoyl)-1,2-dihydro-3H-pyrrolo[1,2-a]pyrrole-1-carboxylate, having a melting point of 82°–82.5° C,
isopropyl 5-(4-chloro-2-thenoyl-1,2-dihydro-3H-pyrrolo[1,2-a]pyrrole-1-carboxylate,
isopropyl 5-(5-chloro-2-thenoyl)-1,2-dihydro-3H-pyrrolo[1,2-a]pyrrole-1-carboxylate,
isopropyl 5-(3-bromo-2-thenoyl)-1,2-dihydro-3H-pyrrolo[1,2-a]pyrrole-1-carboxylate,
isopropyl 5-(4-bromo-2-thenoyl)-1,2-dihydro-3H-pyrrolo[1,2-a]pyrrole-1-carboxylate,
isopropyl 5-(5-bromo-2-thenoyl)-1,2-dihydro-3H-pyrrolo[1,2-a]pyrrole-1-carboxylate,
isopropyl-5-(3-methyl-2-furoyl)-1,2-dihydro-3H-pyrrolo[1,2-a]pyrrole-1-carboxylate, isopropyl-5-(4-methyl-2-furoyl)-1,2-dihydro-3H-pyrrolo[1,2-a]pyrrole-1-carboxylate, isopropyl 5-(5-methyl-2-furoyl)-1,2-dihydro-3H-pyrrolo[1,2-a]pyrrole-1-carboxylate, isopropyl 5-(3-chloro-2-furoyl)-1,2-dihydro-3H-pyrrolo[1,2-a]pyrrole-1-carboxylate, isopropyl 5-(4-chloro-2-furoyl)-1,2-dihydro-3H-pyrrolo[1,2-a]pyrrole-1-carboxylate, isopropyl 5-(5-chloro-2-furoyl)-1,2-dihydro-3H-pyrrolo[1,2-a]pyrrole-1-carboxylate, isopropyl 5-(4-bromo-2-furoyl)-1,2-dihydro-3H-pyrrolo[1,2-a]pyrrole-1-carboxylate and isopropyl 5-(5-bromo-2-furoyl)-1,2-dihydro-3H-pyrrolo[1,2-a]pyrrole-1-carboxylate.

Upon hydrolysis of the isopropyl ester group, in accordance with the methods of Examples 10A or 11, there are obtained the corresponding free acids, namely:

5-(2-furoyl)-1,2-dihydro-3H-pyrrolo[1,2-a]pyrrole-1-carboxylic acid, having a melting point of 184°–184.5° C, 5-(3-methyl-2-thenoyl)-1,2-dihydro-3H-pyrrolo[1,2-a]pyrrole-1-carboxylic acid, 5-(4-methyl-2-thenoyl)-1,2-dihydro-3H-pyrrolo[1,2-a]pyrrole-1-carboxylic acid, 5-(5-methyl-2-thenoyl)-1,2-dihydro-3H-pyrrolo[1,2-a]pyrrole-1-carboxylic acid, having a melting point of 169°–170° C, 5-(4-chloro-2-thenoyl)-1,2-dihydro-3H-pyrrolo[1,2-a]pyrrole-1-carboxylic acid, 5-(5-chloro-2-thenoyl)-1,2-dihydro-3H-pyrrolo[1,2-a]pyrrole-1-carboxylic acid, 5-(3-bromo-2-thenoyl)-1,2-dihydro-3H-pyrrolo[1,2-a]pyrrole-1-carboxylic acid, 5-(4-bromo-2-thenoyl)-1,2-dihydro-3H-pyrrolo[1,2-a]pyrrole-1-carboxylic acid, 5-(5-bromo-2-thenoyl)-1,2-dihydro-3H-pyrrolo[1,2-a]pyrrole-1-carboxylic acid, 5-(3-methyl-2-furoyl)-1,2-dihydro-3H-pyrrolo[1,2-a]pyrrole-1-carboxylic acid, 5-(4-methyl-2-furoyl)-1,2-dihydro-3H-pyrrolo[1,2-a]pyrrole-1-carboxylic acid, 5-(5-methyl-2-furoyl)-1,2-dihydro-3H-pyrrolo[1,2-a]pyrrole-1-carboxylic acid, 5-(3-chloro-2-furoyl)-1,2-dihydro-3H-pyrrolo[1,2-a]pyrrole-1-carboxylic acid, 5-(4-chloro-2-furoyl)-1,2-dihydro-3H-pyrrolo[1,2-a]pyrrole-1-carboxylic acid, 5-(5-chloro-2-furoyl)-1,2-dihydro-3H-pyrrolo[1,2-a]pyrrole-1-carboxylic acid, 5-(4-bromo-2-furoyl)-1,2-dihydro-3H-pyrrolo[1,2-a]pyrrole-1-carboxylic acid, and 5-(5-bromo-2-furoyl)-1,2-dihydro-3H-pyrrolo[1,2-a]pyrrole-1-carboxylic acid.

EXAMPLE 14 A

A 250 ml. 3-necked round bottomed flask containing a magnetic stirring bar and fitted with a calcium chloride filled drying tube, is charged with 3.36 g. of ethanolamine, cooled in an ice bath at 0°–10° C and treated dropwise, with stirring, with 8.7 g. of dimethyl 1,3-acetonedicarboxylate. Methyl 3-carbomethoxymethyl-3-(2'-hydroxyethyl) amino acrylate (III) forms immediately. When the addition is complete, the ice bath is removed and 80 ml. of dry acetonitrile is added. The reaction mixture is then treated dropwise with 6.75 g. of bromoacetaldehyde in 20 ml. of acetonitrile and thereafter heated at reflux temperature for 2 hours. The solvent is then removed under reduced pressure and 200 ml. of methanol and 20 g. of silica gel are added to the residue. This mixture is evaporated to dryness in vacuum and placed on top of a column of 200 g. of silica gel packed in hexane, eluting the column with hexane:ethyl acetate mixtures. The fractions eluted with hexane:ethyl acetate (1:1) afford methyl N-(2-hydroxyethyl)-3-carbomethoxypyrrole-2-acetate (IV, R = H) identical to the product obtained in Example 1.

EXAMPLE 14 B

To a solution of 6 ml. of ethanolamine in 5 ml. of water there is added 1.74 g. of dimethyl 1,3-acetonedicarboxylate. The resultant mixture is rapidly cooled to $-10°$ C and treated dropwise, over a 15 minute period, with stirring, with 1.67 ml. of 1-bromoacetone, whilst maintaining the reaction mixture at a temperature not higher than 40° C. When the addition is completed the dark reaction mixture is stirred for an additional hour at room temperature, and then poured into a mixture of hydrochloric acid-ice, saturated with solid sodium chloride and extracted with ethyl acetate (3 × 100 ml.). The combined organic extract is washed with cold water to neutrality, dried with anhydrous sodium sulfate and evaporated to dryness under reduced pressure. Chromatography of the residue on 30 g. of silica gel, using hexane:ethyl acetate (70:30) as eluant, affords 890 mg. of crystalline methyl N-(2-hydroxyethyl)-3-carbomethoxy-4-methylpyrrole-2-acetate which upon recrystallization from methylene chloride-hexane melts at 78° C and has the following analysis:

Calculated for $C_{12}H_{17}NO_5$: C, 56.45; H, 6.71; Found: C, 56.41; H, 6.73.

In a similar manner but using a stoichiometric equivalent of 1-bromo-2-butanone, 1-bromo-2-pentanone, and 1-bromo-2-hexanone in place of 1-bromoacetone there are respectively obtained:

methyl N-(2-hydroxyethyl)-3-carbomethoxy-4-ethylpyrrole-2-acetate, methyl N-(2-hydroxyethyl)-3-carbomethoxy-4-propylpyrrole-2-acetate and methyl N-(2-hydroxyethyl)-3-carbomethoxy-4-butylpyrrole-2-acetate.

EXAMPLE 15

By following the method of Example 2, methyl N-(2-hydroxyethyl)-3-carbomethoxy-4-methylpyrrole-2-acetate (IV, R = CH₃) is converted into methyl N-(2-mesyloxyethyl)-3-carbomethoxy-4-methylpyrrole-2-acetate and then cyclized with sodium hydride in dimethylformamide, in accordance with the method of Example 8, to afford dimethyl 1,2-dihydro-6-methyl-3H-pyrrolo[1,2-a]pyrrole-1,7-dicarboxylate.

Upon hydrolysis of the latter compound with potassium hydroxide, in accordance with the method of Example 4 followed by selective esterification at C-1 and decarboxylation at C-7, in accordance with the methods of Examples 5 and 7, respectively, there are successively obtained 1,2-dihydro-6-methyl-3H-pyrrolo[1,2-a]pyrrole-1,7-dicarboxylic acid, isopropyl 1,2-dihydro-6-methyl-3H-pyrrolo[1,2-a]pyrrole-1-carboxylate-7-carboxylic acid and isopropyl 1,2-dihydro-6-methyl-3H-pyrrolo[1,2-a]pyrrole-1-carboxylate (X, R = CH₃, R² = iC₃H₇).

In a similar manner, substituting methyl N-(2-hydroxyethyl)-3-carbomethoxy-4-ethylpyrrole-2-acetate, methyl N-(2-hydroxyethyl)-3-carbomethoxy-4-propylpyrrole-2-acetate and methyl N-(2-hydroxyethyl)-3-carbomethoxy-4-butylpyrrole-2-acetate for methyl N-

(2-hydroxyethyl)-3-carbomethoxy-4-methylpyrrole-2-acetate there are respectively obtained as final products:

- isopropyl 1,2-dihydro-6-ethyl-3H-pyrrolo[1,2-a]pyrrole-1-carboxylate,
- isopropyl 1,2-dihydro-6-propyl-3H-pyrrolo[1,2-a]pyrrole-1-carboxylate and
- isopropyl 1,2-dihydro-6-butyl-3H-pyrrolo[1,2-a]pyrrole-1-carboxylate.

EXAMPLE 16

In accordance with the method of Example 9, isopropyl 1,2-dihydro-6-methyl-3H-pyrrolo[1,2-a]pyrrole-1-carboxylate is condensed with N,N-dimethylthiophene-2-carboxamide to produce isopropyl 5-(2-thenoyl)-1,2-dihydro-6-methyl-3H-pyrrolo[1,2-a]pyrrole-1-carboxylate (XI, $R = CH_3$, $R^1 = H$, $R^2 = iC_3H_7$, $X = S$), having a melting point of 102.5° C.

In a similar manner but using the N,N-dimethylthiophene- or furan-2-carboxamides listed in Example 13 in place of N,N-dimethylthiophene-2-carboxamide, there are respectively obtained:

- isopropyl 5-(2-furoyl)-1,2-dihydro-6-methyl-3H-pyrrolo[1,2-a]pyrrole-1-carboxylate,
- isopropyl 5-(3-methyl-2-thenoyl)-1,2-dihydro-6-methyl-3H-pyrrolo[1,2-a]pyrrole-1-carboxylate,
- isopropyl 5-(4-methyl-2-thenoyl)-1,2-dihydro-6-methyl-3H-pyrrolo[1,2-a]pyrrole-1-carboxylate,
- isopropyl 5-(5-methyl-2-thenoyl)-1,2-dihydro-6-methyl-3H-pyrrolo[1,2-a]pyrrole-1-carboxylate,
- isopropyl 5-(4-chloro-2-thenoyl)-1,2-dihydro-6-methyl-3H-pyrrolo[1,2-a]pyrrole-1-carboxylate,
- isopropyl 5-(5-chloro-2-thenoyl)-1,2-dihydro-6-methyl-3H-pyrrolo[1,2-a]pyrrole-1-carboxylate,
- isopropyl 5-(3-bromo-2-thenoyl)-1,2-dihydro-6-methyl-3H-pyrrolo[1,2-a]pyrrole-1-carboxylate,
- isopropyl 5-(4-bromo-2-thenoyl)-1,2-dihydro-6-methyl-3H-pyrrolo[1,2-a]pyrrole-1-carboxylate,
- isopropyl 5-(5-bromo-2-thenoyl)-1,2-dihydro-6-methyl-3H-pyrrolo[1,2-a]pyrrole-1-carboxylate,
- isopropyl 5-(3-methyl-2-furoyl)-1,2-dihydro-6-methyl-3H-pyrrolo[1,2-a]pyrrole-1-carboxylate,
- isopropyl 5-(4-methyl-2-furoyl)-1,2-dihydro-6-methyl-3H-pyrrolo[1,2-a]pyrrole-1-carboxylate,
- isopropyl 5-(5-methyl-2-furoyl)-1,2-dihydro-6-methyl-3H-pyrrolo[1,2-a]pyrrole-1-carboxylate,
- isopropyl 5-(3-chloro-2-furoyl)-1,2-dihydro-6-methyl-3H-pyrrolo[1,2-a]pyrrole-1-carboxylate,
- isopropyl 5-(4-chloro-2-furoyl)-1,2-dihydro-6-methyl-3H-pyrrolo[1,2-a]pyrrole-1-carboxylate,
- isopropyl 5-(5-chloro-2-furoyl)-1,2-dihydro-6-methyl-3H-pyrrolo[1,2-a]pyrrole-1-carboxylate,
- isopropyl 5-(4-bromo-2-furoyl)-1,2-dihydro-6-methyl-3H-pyrrolo[1,2-a]pyrrole-1-carboxylate and
- isopropyl 5-(5-bromo-2-furoyl)-1,2-dihydro-6-methyl-3H-pyrrolo[1,2-a]pyrrole-1-carboxylate.

Likewise, the remaining final compounds obtained in Example 15 are converted into the corresponding 5-furoyl or thenoyl substituted derivatives. Representative compounds thus obtained are:

- isopropyl 5-(2-thenoyl)-1,2-dihydro-6-ethyl-3H-pyrrolo[1,2-a]pyrrole-1-carboxylate,
- isopropyl 5-(2-furoyl)-1,2-dihydro-6-propyl-3H-pyrrolo[1,2-a]pyrrole-1-carboxylate,
- isopropyl 5-(3-methyl-2-thenoyl)-1,2-dihydro-6-butyl-3H-pyrrolo[1,2-a]pyrrole-1-carboxylate,
- isopropyl 5-(4-chloro-2-thenoyl)-1,2-dihydro-6-ethyl-3H-pyrrolo[1,2-a]pyrrole-1-carboxylate,
- isopropyl 5-(5-methyl-2-furoyl)-1,2-dihydro-6-propyl-3H-pyrrolo[1,2-a]pyrrole-1-carboxylate and
- isopropyl 5-(3-chloro-2-furoyl)-1,2-dihydro-6-butyl-3H-pyrrolo[1,2-a]pyrrole-1-carboxylate.

EXAMPLE 17

A solution of 500 mg. of isopropyl 5-(2-thenoyl)-1,2-dihydro-6-methyl-3H-pyrrolo[1,2-a]pyrrole-1-carboxylate in 15 ml. of methanol is treated with a solution of 1.05 g. of potassium carbonate in 8 ml. of water. The reaction mixture is refluxed under nitrogen atmosphere for 3 hours, cooled, and evaporated to dryness. The residue is taken up in 10 ml. of 10% aqueous hydrochloric acid and 50 ml. of water and the resultant mixture extracted with ethyl acetate (3 × 50 ml.). The combined extracts are dried over magnesium sulfate and evaporated to dryness under reduced pressure, to give 5-(2-thenoyl)-1,2-dihydro-6-methyl-3H-pyrrolo[1,2-a]pyrrole-1-carboxylic acid [(A), $R = CH_3$, $R^1 = H$, $X = S$], having a melting point of 166° C.

In a similar manner, or alternatively by the hydrolysis method of Example 10 A, the remaining isopropyl ester compounds obtained in Example 16 are converted into the corresponding free acids, namely:

- 5-(2-furoyl)-1,2-dihydro-6-methyl-3H-pyrrolo[1,2-a]pyrrole-1-carboxylic acid,
- 5-(3-methyl-2-thenoyl)-1,2-dihydro-6-methyl-3H-pyrrolo[1,2-a]pyrrole-1-carboxylic acid,
- 5-(4-methyl-2-thenoyl)-1,2-dihydro-6-methyl-3H-pyrrolo[1,2-a]pyrrole-1-carboxylic acid,
- 5-(5-methyl-2-thenoyl)-1,2-dihydro-6-methyl-3H-pyrrolo[1,2-a]pyrrole-1-carboxylic acid,
- 5-(4-chloro-2-thenoyl)-1,2-dihydro-6-methyl-3H-pyrrolo[1,2-a]pyrrole-1-carboxylic acid,
- 5-(5-chloro-2-thenoyl)-1,2-dihydro-6-methyl-3H-pyrrolo[1,2-a]pyrrole-1-carboxylic acid,
- 5-(3-bromo-2-thenoyl)-1,2-dihydro-6-methyl-3H-pyrrolo[1,2-a]pyrrole-1-carboxylic acid,
- 5-(4-bromo-2-thenoyl)-1,2-dihydro-6-methyl-3H-pyrrolo[1,2-a]pyrrole-1-carboxylic acid,
- 5-(5-bromo-2-thenoyl)-1,2-dihydro-6-methyl-3H-pyrrolo[1,2-a]pyrrole-1-carboxylic acid,
- 5-(3-methyl-2-furoyl)-1,2-dihydro-6-methyl-3H-pyrrolo[1,2-a]pyrrole-1-carboxylic acid,
- 5-(4-methyl-2-furoyl)-1,2-dihydro-6-methyl-3H-pyrrolo[1,2-a]pyrrole-1-carboxylic acid,
- 5-(5-methyl-2-furoyl)-1,2-dihydro-6-methyl-3H-pyrrolo[1,2-a]pyrrole-1-carboxylic acid,
- 5-(3-chloro-2-furoyl)-1,2-dihydro-6-methyl-3H-pyrrolo[1,2-a]pyrrole-1-carboxylic acid,
- 5-(4-chloro-2-furoyl)-1,2-dihydro-6-methyl-3H-pyrrolo[1,2-a]pyrrole-1-carboxylic acid,
- 5-(5-chloro-2-furoyl)-1,2-dihydro-6-methyl-3H-pyrrolo[1,2-a]pyrrole-1-carboxylic acid,
- 5-(4-bromo-2-furoyl)-1,2-dihydro-6-methyl-3H-pyrrolo[1,2-a]pyrrole-1-carboxylic acid,
- 5-(5-bromo-2-furoyl)-1,2-dihydro-6-methyl-3H-pyrrolo[1,2-a]pyrrole-1-carboxylic acid,
- 5-(2-thenoyl)-1,2-dihydro-6-ethyl-3H-pyrrolo[1,2-a]pyrrole-1-carboxylic acid,
- 5-(2-furoyl)-1,2-dihydro-6-propyl-3H-pyrrolo[1,2-a]pyrrole-1-carboxylic acid,
- 5-(3-methyl-2-thenoyl)-1,2-dihydro-6-butyl-3H-pyrrolo[1,2-a]pyrrole-1-carboxylic acid,
- 5-(4-chloro-2-thenoyl)-1,2-dihydro-6-ethyl-3H-pyrrolo[1,2-a]pyrrole-1-carboxylic acid,
- 5-(5-methyl-2-furoyl)-1,2-dihydro-6-propyl-3H-pyrrolo[1,2-a]pyrrole-1-carboxylic acid and 5-(3-chloro-2-furoyl)-1,2-dihydro-6-butyl-3H-pyrrolo[1,2-a]pyrrole-1-carboxylic acid.

EXAMPLE 18

A solution of 232.5 mg. of N,N-dimethylthiophene-3-carboxamide and 0.15 ml. of phosphororus oxychloride in 2 ml. of 1,2-dichloroethane is refluxed for 30 minutes. To this solution is added a solution of 181 mg. of isopropyl 1,2-dihydro-3H-pyrrolo[1,2-a]pyrrole-1-carboxylate in 2 ml. of 1,2-dichloroethane. The reaction mixture is refluxed under an argon atmosphere for 8 hours, treated with 450 mg. of sodium acetate and refluxed for a further 5 hours. The resultant mixture is then evaporated to dryness and the residue is chromatographed on 12 g. of silica gel, eluting with hexane:ethyl acetate (3:1), thus obtaining isopropyl 5-(3-thenoyl)-1,2-dihydro-3H-pyrrolo[1,2-a]pyrrole-1-carboxylate (XII, R = H, $R^2$ = $iC_3H_7$, X = S).

In a similar manner isopropyl 1,2-dihydro-6-methyl-3H-pyrrolo[1,2-a]pyrrole-1-carboxylate and isopropyl 1,2-dihydro-6-propyl-3H-pyrrolo[1,2-a]pyrrole-1-carboxylate are converted respectively into isopropyl 5-(3-thenoyl)-1,2-dihydro-6-methyl-3H-pyrrolo[1,2-a]pyrrole-1-carboxylate and isopropyl 5-(3-thenoyl)-1,2-dihydro-6-propyl-3H-pyrrolo[1,2-a]pyrrole-1-carboxylate.

By the same method, substituting N,N-dimethylfuran-3-carboxamide for N,N-dimethylthiophene-3-carboxamide there are obtained the corresponding 5-(3-furoyl) derivatives, namely:

isopropyl 5-(3-furoyl)-1,2-dihydro-3H-pyrrolo[1,2-a]pyrrole-1-carboxylate, an oil, having the following physical constants:

|  | MeOH |
|---|---|
| U.V. | $\lambda_{max}$ 222, 244–277 (shoulder), 314 nm ($\epsilon$ 6750, 4250, 14800); |
| I.R. | $CHCl_3$ $\nu_{max}$ 1730, 1610, 1560 $cm^{-1}$; |
| N.M.R. | $CDCl_3$ $\delta_{TMS}$ 1.23 [d, 6H, J = 6 Hz; $(CH_3)_2CH$], 2.50–3.00 (m, 2H), 3.92 (dd, 2H, $J_{AX}$ = 6 Hz, $J_{BX}$ = 7 Hz; H-1), 4.10–4.60 (m, 2H), 4.95 [sept., 1H, J = 6 Hz; $(CH_3)_2CH$], 5.95 (d, 1H, J = 4 Hz; H-7), 6.78 (m, 1H), 6.83 (d, 1H, J = 4 Hz; H-6), 7.30 (m, 1H), 7.83 ppm (m, 1H); |
| M.S. m/e | 270 ($M^+$), | isopropyl 5-(3-furoyl)-1,2-dihydro-6-methyl-3H-pyrrolo[1,2-a]pyrrole-1-carboxylate and
isopropyl 5-(3-furoyl)-1,2-dihydro-6-propyl-3H-pyrrolo[1,2-a]pyrrole-1-carboxylate.

EXAMPLE 19

A solution of 300 mg. of isopropyl 5-(3-thenoyl)-1,2-dihydro-3H-pyrrolo[1,2-a]pyrrole-1-carboxylate in 30 ml. of 50% aqueous methanol containing 1% of potassium hydroxide is refluxed under an atmosphere of nitrogen for 2 hours. The methanol is then removed under reduced pressure and the basic solution which remains is diluted with water and extracted with chloroform to remove any unsaponifiable product. The aqueous alkaline phase is acidified with 20% hydrochloric acid and extracted three times with ethyl acetate. The combined extracts are dried over sodium sulfate and evaporated to dryness under reduced pressure, thus obtaining 250 mg. of crude 5-(3-thenoyl)-1,2-dihydro-3H-pyrrolo[1,2-a]pyrrole-1-carboxylic acid, [(B), R = H, X = S].

By the same method, the remaining compounds obtained in Example 18 are converted into the free acids, namely:

5-(3-thenoyl)-1,2-dihydro-6-methyl-3H-pyrrolo[1,2-a]pyrrole-1-carboxylic acid,
5-(3-thenoyl)-1,2-dihydro-6-propyl-3H-pyrrolo[1,2-a]pyrrole-1-carboxylic acid,
5-(3-furoyl)-1,2-dihydro-3H-pyrrolo[1,2-a]pyrrole-1-carboxylic acid, having a melting point of 156° C,
5-(3-furoyl)-1,2-dihydro-6-methyl-3H-pyrrolo[1,2-a]pyrrole-1-carboxylic acid and
5-(3-furoyl)-1,2-dihydro-6-propyl-3H-pyrrolo[1,2-a]pyrrole-1-carboxylic acid.

EXAMPLE 20

A solution of 200 mg. of 5-(2-furoyl)-1,2-dihydro-3H-pyrrolo[1,2-a]pyrrole-1-carboxylic acid in 5 ml. of dichloromethane is treated with an excess of ethereal diazomethane, and the reaction mixture is maintained at room temperature for 30 minutes. The solvents and excess reagent are eliminated under reduced pressure and the residue crystallized from ethyl acetate-methanol, to yield methyl 5-(2-furoyl)-1,2-dihydro-3H-pyrrolo[1,2-a]pyrrole-1-carboxylate.

Likewise but using diazoethane and diazopropane is place of diazomethane there are respectively obtained ethyl 5-(2-furoyl)-1,2-dihydro-3H-pyrrolo[1,2-a]pyrrole-1-carboxylate and propyl 5-(2-furoyl)-1,2-dihydro-3H-pyrrolo[1,2,-a]pyrrole-1-carboxylate.

In a similar manner, the remaining free acids obtained in Examples 10 A, 10 B-1 (and 10 B-2), 13 and the acids of Examples 17 and 19 are converted into the corresponding methyl, ethyl and propyl esters. Representative compounds thus-obtained are:

methyl 5-(2-thenoyl)-1,2-dihydro-3H-pyrrolo-[1,2-a]pyrrole-1-carboxylate,
ethyl 5-(2-thenoyl)-1,2-dihydro-3H-pyrrolo-[1,2-a]pyrrole-1-carboxylate,
propyl 5-(2-thenoyl)-1,2-dihydro-3H-pyrrolo-[1,2-a]pyrrole-1-carboxylate, and
the methyl ethyl and propyl esters of (1)-5-(2-thenoyl)-1,2-dihydro-3H-pyrrolo-[1,2-a]pyrrole-1-carboxylic acid.

EXAMPLE 21

A solution of 300 mg. of 5-(2-thenoyl)-1,2-dihydro-3H-pyrrolo[1,2-a]pyrrole-1-carboxylic acid in 5 ml. of isoamyl alcohol is saturated with hydrogen chloride. After 24 hours, the excess alcohol is distilled off in vacuum and the residue purified by chromatography on alumina to yield isoamyl 5-(2-thenoyl)-1,2-dihydro-3H-pyrrolo[1,2-a]pyrrole-1-carboxylate.

Likewise other esters, e.g., pentyl, hexyl, octyl, nonyl, dodecyl and the like, of 5-(2-thenoyl)-1,2-dihydro-3H-pyrrolo[1,2-a]pyrrole-1-carboxylic acid are obtained by substituting other alcohols, e.g., pentyl, hexyl, octyl, nonyl, dodecyl alcohol and the like, for isoamyl alcohol.

By the same method the free acid compounds obtained in Examples 10 B-1, 13, 17 and 19 are esterified with the appropriate alcohol to produce the corresponding esters, e.g., isoamyl 5-(2-furoyl)-1,2-dihydro-3H-pyrrolo[1,2-a]pyrrole-1-carboxylate,
pentyl 5-(4-methyl-2-thenoyl)-1,2-dihydro-3H-pyrrolo[1,2-a]pyrrole-1-carboxylate,
hexyl 5-(5-chloro-2-thenoyl)-1,2-dihydro-3H-pyrrolo[1,2-a]pyrrole-1-carboxylate, isoamyl 5-(4-bromo-2-thenoyl)-1,2-dihydro-3H-pyrrolo[1,2-a]pyrrole-1-carboxylate,
octyl 5-(2-furoyl)-1,2-dihydro-3H-pyrrolo[1,2-a]pyrrole-1-carboxylate,
nonyl 5-(3-methyl-2-furoyl)-1,2-dihydro-3H-pyrrolo[1,2-a]pyrrole-1-carboxylate,
dodecyl 5-(3-chloro-2-furoyl)-1,2-dihydro-3H-pyrrolo[1,2-a]pyrrole-1-carboxylate,
hexyl 5-(4-chloro-2-thenoyl)-1,2-dihydro-6-methyl-3H-pyrrolo[1,2-a]pyrrole-1-carboxylate,
isoamyl 5-(2-thenoyl)-1,2-dihydro-6-ethyl-3H-pyrrolo[1,2-a]pyrrole-1-carboxylate and
octyl 5-(3-furoyl)-1,2-dihydro-3H-pyrrolo[1,2-a]pyrrole-1-carboxylate.

EXAMPLE 22

To a solution of 300 mg. of 5-(2-thenoyl)-1,2-dihydro-3H-pyrrolo[1,2-a]pyrrole-1-carboxylic acid in 5 ml. of methanol is added 1 molar equivalent of sodium hydroxide, in the form of a 0.1N solution. The solvent is then evaporated under reduced pressure and the residue taken up in 2 ml. of methanol, followed by precipitation with ether, to yield crude sodium 5-(2-thenoyl)-1,2-dihydro-3H-pyrrolo[1,2-a]pyrrole-1-carboxylate which can be crystallized from isopropanol.

Likewise other salts, e.g., ammonium and potassium, of 5-(2-thenoyl)-1,2-dihydro-3H-pyrrolo[1,2-a]pyrrole-1-carboxylic acid are prepared by substituting ammonium hydroxide and potassium hydroxide for sodium hydroxyde.

In a similar manner, the 5-substituted 1,2-dihydro-3H-pyrrolo[1,2-a]pyrrole-1-carboxylic acid compounds obtained in Examples 10 B-1 (and 10 B-2) 13, 17 and 19 can be converted into the corresponding sodium, potassium and ammonium salts.

Representative compounds thus obtained are:
sodium (1)-5-(2-thenoyl)-1,2-dihydro-3H-pyrrolo[1,2-a]pyrrole-1-carboxylate,
sodium 5-(2-furoyl)-1,2-dihydro-3H-pyrrolo[1,2-a]pyrrole-1-carboxylate,
sodium 5-(4-methyl-2-thenoyl)-1,2-dihydro-3H-pyrrolo[1,2-a]pyrrole-1-carboxylate,
potassium 5-(4-chloro-2-thenoyl)-1,2-dihydro-3H-pyrrolo[1,2-a]pyrrole-1-carboxylate,
potassium 5-(5-bromo-2-thenoyl)-1,2-dihydro-3H-pyrrolo[1,2-a]pyrrole-1-carboxylate,
sodium 5-(3-methyl-2-furoyl)-1,2-dihydro-3H-pyrrolo[1,2-a]pyrrole-1-carboxylate,
ammonium 5-(2-furoyl)-1,2-dihydro-3H-pyrrolo[1,2-a]pyrrole-1-carboxylate,
ammonium 5-(3-chloro-2-furoyl)-1,2-dihydro-3H-pyrrolo[1,2-a]pyrrole-1-carboxylate,
sodium 5-(4-methyl-2-thenoyl)-1,2-dihydro-6-ethyl-3H-pyrrolo[1,2-a]pyrrole-1-carboxylate,
potassium 5-(5-chloro-2-thenoyl)-1,2-dihydro-6-methyl-3H-pyrrolo[1,2-a]pyrrole-1-carboxylate,
ammonium 5-(3-thenoyl)-1,2-dihydro-3H-pyrrolo[1,2-a]pyrrole-1-carboxylate and
sodium 5-(3-furoyl)-1,2-dihydro-3H-pyrrolo[1,2-a]pyrrole-1-carboxylate.

EXAMPLE 23

To a solution of 237 mg. of 5-(2-thenoyl)-1,2-dihydro-3H-pyrrolo[1,2-a]pyrrole-1-carboxylic acid in 8 ml. of methanol is added 1 molar equivalent of potassium hydroxide, in the form of a 0.1N solution to yield a solution containing potassium 5-(2-thenoyl)-1,2-dihydro-3H-pyrrolo[1,2-a]pyrrole-1-carboxylate. A solution of 50 mg. of calcium carbonate dissolved in the minimum amount of 1N hydrochloric acid necessary to effect solution of the calcium carbonate, is buffered with 100 mg. of solid ammonium chloride, followed by the further addition of 5 ml. of water. The thus obtained buffered calcium solution is then added to the solution of potassium 5-(2-thenoyl)-1,2-dihydro-3H-pyrrolo[1,2-a]pyrrole-1-carboxylate and the precipitate which forms is collected by filtration, washed with water and air dried, to yield calcium 5-(2-thenoyl)-1,2-dihydro-3H-pyrrolo[1,2-a]pyrrole-1-carboxylate.

Likewise magnesium 5-(2-thenoyl)-1,2-dihydro-3H-pyrrolo[1,2-a]pyrrole-1-carboxylate is prepared by substituting magnesium carbonate for calcium carbonate.

Similarly, by substituting
(1)-5-(2-thenoyl)-1,2-dihydro-3H-pyrrolo-[1,2-a]pyrrole-1-carboxylic acid,
5-(2-furoyl)-1,2-dihydro-3H-pyrrolo[1,2-a]pyrrole-1-carboxylic acid,
5-(4-chloro-2-thenoyl)-1,2-dihydro-3H-pyrrolo[1,2-a]pyrrole-1-carboxylic acid,
5-(3-methyl-2-thenoyl)-1,2-dihydro-3H-pyrrolo[1,2-a]pyrrole-1-carboxylic acid,
5-(5-bromo-2-furoyl)-1,2-dihydro-6-methyl-3H-pyrrolo[1,2-a]pyrrole-1-carboxylic acid, and
5-(3-chloro-2-furoyl)-1,2-dihydro-6-ethyl-3H-pyrrolo[1,2-a]pyrrole-1-carboxylic acid, for 5-(2-thenoyl)-1,2-dihydro-3H-pyrrolo[1,2-a]pyrrole-1-carboxylic acid there are obtained the corresponding calcium and magnesium salts.

EXAMPLE 24

To a solution of 237 mg. of 5-(2-thenoyl)-1,2-dihydro-3H-pyrrolo[1,2-a]pyrrole-1-carboxylic acid in 8 ml. of methanol is added 1 molar equivalent of potassium hydroxide, in the form of a 0.1N solution. The solvent is stripped and the residue is dissolved in 5 ml. of water. The thus obtained aqueous solution of potassium 5-(2-thenoyl)-1,2-dihydro-3H-pyrrolo[1,2-a]pyrrole-1-carboxylate is added to a solution of 110 mg. of cupric nitrate trihydrate in 5 ml. of water. The formed precipitate is collected, washed with water and air dried, thus obtaining copper 5-(2-thenoyl)-1,2-dihydro-3H-pyrrolo[1,2-a]pyrrole-1-carboxylate.

In a similar manner the free acid compounds obtained in Examples 10 B-1 (and 10 B-2), 13, 17 and 19 can be converted into the corresponding copper salts.

EXAMPLE 25

A solution of 237 mg. of 5-(2-thenoyl)-1,2-dihydro-3H-pyrrolo[1,2-a]pyrrole-1-carboxylic acid in 15 ml. of hot benzene is treated with 59 mg. of isopropylamine. The solution is allowed to cool to room temperature and the product filtered off, washed with ether and dried, to yield the isopropylamine salt of 5-(2-thenoyl)-1,2-dihydro-3H-pyrrolo[1,2-a]pyrrole-1-carboxylic acid.

Likewise other amine salts, e.g., diethylamine, ethanolamine, piperidine, tromethamine, choline and caffeine salts of 5-(2-thenoyl)-1,2-dihydro-3H-pyrrolo[1,2-a]pyrrole-1-carboxylic acid are prepared by substituting each of the respective amines for isopropylamine.

In similar manner the free acid compounds obtained in Examples 10 B-1 (or 10 B-2), 13, 17 and 19 can be converted into the corresponding isopropylamine, diethylamine, ethanolamine, piperidine, tromethamine, choline and caffeine salts.

EXAMPLE 26

| Ingredients | Quantity per tablet, mgs. |
|---|---|
| 5-(2-thenoyl)-1,2-dihydro-3H-pyrrolo-[1,2-a]pyrrole-1-carboxylic acid | 25 |
| cornstarch | 20 |
| lactose, spray-dried | 153 |
| magnesium stearate | 2 |

The above ingredients are thoroughly mixed and pressed into single scored tablets.

EXAMPLE 27

| Ingredients | Quantity per tablet, mgs. |
|---|---|
| 5-(2-thenoyl)-1,2-dihydro-3H-pyrrolo-[1,2-a]pyrrole-1-carboxylic acid | 200 |
| cornstarch | 50 |
| lactose | 145 |
| magnesium stearate | 5 |

The above ingredients are mixed intimately and pressed into single scored tablets.

100 Mg. of (1)-5-(2-thenoyl)-1,2-dihydro-3H-pyrrolo[1,2-a]pyrrole-1-carboxylic acid is substituted for the 200 mg. of the (dl) compound of the above composition.

EXAMPLE 28

| Ingredients | Quantity per capsule, mgs. |
|---|---|
| potassium 5-(2-thenoyl)-1,2-dihydro-3H-pyrrolo-[1,2-a]pyrrole-1-carboxylate | 108 |
| lactose | 15 |
| cornstarch | 25 |
| magnesium stearate | 2 |

The above ingredients are mixed and introduced into a hard-shell gelatin capsule.

EXAMPLE 29

| Ingredients | Quantity per capsule, mgs. |
|---|---|
| calcium 5-(2-thenoyl)-1,2-dihydro-3H-pyrrolo-[1,2-a]pyrrole-1-carboxylate | 115 |
| lactose | 93 |
| cornstarch | 40 |
| magnesium stearate | 2 |

The above ingredients are mixed and introduced into a hard-shell gelatin capsule.

EXAMPLE 30

| Ingredients | Quantity per tablet, mgs. |
|---|---|
| isopropylammonium 5-(2-thenoyl)-1,2-dihydro-3H-pyrrolo-[1,2-a]pyrrole-1-carboxylate | 245 |
| cornstarch | 75 |
| lactose | 175 |
| magnesium stearate | 5 |

The above ingredients are mixed intimately and pressed into single scored tablets.

EXAMPLE 31

| Ingredients | Quantity per capsule, mgs. |
|---|---|
| methyl 5-(2-thenoyl)-1,2-dihydro-3H-pyrrolo-[1,2-a]pyrrole-1-carboxylate | 25 |
| lactose | 125 |

The above ingredients are mixed and introduced into a No. 1 hard-shell gelatin capsule.

EXAMPLE 32

| Ingredients | Quantity per tablet, mgs. |
|---|---|
| 5-(2-thenoyl)-1,2-dihydro-3H-pyrrolo-[1,2-a]pyrrole-1-carboxylic acid | 300 |
| sucrose | 300 |

The above ingredients are thoroughly mixed and processed into single scored tablets, one tablet being administered every 3 to 4 hours.

EXAMPLE 33

| Ingredients | Quantity per tablet, mgs. |
|---|---|
| isoamyl 5-(2-thenoyl)-1,2-dihyro-3H-pyrrolo-[1,2-a]pyrrole-1-carboxylate | 254 |
| cornstarch | 50 |
| lactose | 190 |
| magnesium stearate | 6 |

The above ingredients are mixed intimately and pressed into single scored tablets.

EXAMPLE 34

| Ingredients | Quantity per capsule, mgs. |
|---|---|
| 5-(2)-thenoyl-1,2-dihydro-3H-pyrrolo-[1,2-a]pyrrole-1-carboxylic acid | 100 |
| lactose | 148 |
| dextrose | 2 |

The above ingredients are mixed and introduced into a hard-shell gelatin capsule.

50 Mg. of (1)-5-(2-thenoyl)-1,2-dihydro-3H-pyrrolo-[1,2-a]pyrrole-1-carboxylic acid is substituted for the 100 mg. of the (dl) compound of the above composition.

EXAMPLE 35

| Ingredients | Quantity per capsule, mgs. |
|---|---|
| methyl 5-(2-thenoyl)-1,2-dihydro-3H-pyrrolo-[1,2-a]pyrrole-1-carboxylate | 158 |
| lactose | 92 |

The above ingredients are mixed and introduced into a hard-shell gelatin capsule.

EXAMPLE 36

| Ingredients | Quantity per tablet, mgs. |
|---|---|
| isoamyl 5-(2-thenoyl)-1,2-dihydro-3H-pyrrolo-[1,2-a]pyrrole-1-carboxylate | 127 |
| lactose | 91 |
| cornstarch | 25 |

EXAMPLE 36-continued

| Ingredients | Quantity per tablet, mgs. |
|---|---|
| magnesium stearate | 2 |
| gelatin | 5 |

The above ingredients are mixed and pressed into single scored tablets.

EXAMPLE 37

| Ingredients | Quantity per tablet, mgs. |
|---|---|
| calcium 5-(2-thenoyl)-1,2-dihydro-3H-pyrrolo-[1,2-a]pyrrole-1-carboxylate | 230 |
| cornstarch (paste) | 40 |
| cornstarch | 50 |
| magnesium stearate | 2 |
| lactose | 178 |

The above ingredients are thoroughly mixed and pressed into single scored tablets.

EXAMPLE 38

| Ingredients | Quantity per tablet, mgs. |
|---|---|
| potassium 5-(2-thenoyl)-1,2-dihydro-3H-pyrrolo-[1,2-a]pyrrole-1-carboxylate | 217 |
| cornstarch | 50 |
| magnesium stearate | 2 |
| gelatin | 226 |
| lactose | 5 |

The above ingredients are mixed intimately and pressed into single scored tablets.

EXAMPLE 39

| Ingredients | Quantity per capsule, mgs. |
|---|---|
| isopropylammonium 5-(2-thenoyl)-1,2-dihydro-3H-pyrrolo-[1,2-a]pyrrile-1-carboxylate | 122 |
| cornstarch | 30 |
| lactose | 98 |

The above ingredients are mixed and introduced into a hard-shell gelatin capsule.

EXAMPLE 40

| Ingredients | Quantity per capsule, mgs. |
|---|---|
| isoamyl 5-(2-thenoyl)-1,2-dihydro-3H-pyrrolo-[1,2-a]pyrrole-1-carboxylate | 32 |
| lactose | 101 |
| cornstarch | 15 |
| magnesium stearate | 2 |

The above ingredients are mixed and introduced into a hard-shell gelatin capsule.

EXAMPLE 41

An injectable preparation buffered to a pH of 7 is prepared having the following composition:

| | |
|---|---|
| 5-(2-thenoyl)-1,2-dihydro-3H-pyrrolo-[1,2-a]pyrrole-1-carboxylic acid | 0.2 g |
| $K_2HPO_4$ buffer (0.4 M solution) | 2 ml. |
| KOH (1N) | q.s. to pH7 |
| water (distilled sterile) | q.s. to 20 ml. |

0.1 G. of (l)-5-(2-thenoyl)-1,2-dihydro-3H-pyrrolo-[1,2-a]pyrrole-1-carboxylic acid is substituted for the 0.2 g. of the (dl) compound of the above composition.

EXAMPLE 42

A suppository totaling 2.8 grams is prepared having the following composition:

| | |
|---|---|
| 5-(2-thenoyl)-1,2-dihydro-3H-pyrrolo-[1,2-a]pyrrole-1-carboxylic acid | 25 mg. |
| Witepsol H-15 (triglycerides of saturated vegetable fatty acids; a product of Riches-Nelson, Inc., New York, N.Y.) | balance |

12.5 Mg. of (l)-5-(2-thenoyl)-1,2-dihydro-3H-pyrrolo-[1,2-a]pyrrole-1-carboxylic acid is substituted for the 25 mg. of the (dl) compound of the above composition.

EXAMPLE 43

An oral suspension for pediatric use is prepared having the following composition:

| | |
|---|---|
| (1)-5-(2-thenoyl)-1,2-dihydro-3H-pyrrolo-[1,2-a]pyrrole-1-carboxylic acid | 0.1 g. |
| fumaric acid | 0.5 g. |
| sodium chloride | 2.0 g. |
| methyl paraben | 0.1 g. |
| granulated sugar | 25.5 g. |
| sorbitol (70% solution) | 12.85 g. |
| Veegum K (Vanderbilt Co.) | 1.0 g. |
| flavoring | 0.035 ml. |
| colorings | 0.5 mg. |
| distilled water | q.s. to 100 ml. |

0.05 G. of (l)-5-(2-thenoyl)-1,2-dihydro-3H-pyrrolo-[1,2-a]pyrrole-1-carboxylic acid is substituted for the 0.1 g. of the (dl) compound of the above composition.

EXAMPLES 44–45

Powdered top dressings for veterinary use are prepared having the following compositions:

| | Ex. 44 | Ex. 45 |
|---|---|---|
| 5-(2-thenoyl)-1,2-dihydro-3H-pyrrolo-[1,2-a]pyrrole-1-carboxylic acid | 0.1 g. | 1.2 g. |
| sucrose | 5.7 g. | 3.7 g. |
| polyvinyl pyrrolidone | 0.3 g. | 0.3 g. |

0.05 G. of (l)-5-(2-thenoyl)-1,2-dihydro-3H-pyrrolo-[1,2-a]pyrrole-1-carboxylic acid is substituted for the 0.1 g. of the (dl) compound of the composition of Example 44.

0.6 G. of (l)-5-(2-thenoyl)-1,2-dihydro-3H-pyrrolo-[1,2-a]pyrrole-1-carboxylic acid is substituted for the 1.2 g. of the (dl) compound of the composition of Example 45.

What is claimed is:

1. A compound selected from the group of those represented by the formulas:

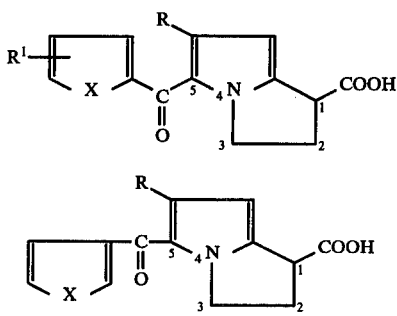

and the pharmaceutically acceptable, non-toxic alkyl esters having from one to 12 carbon atoms and salts thereof, wherein X is oxygen or sulphur, R is hydrogen or a lower alkyl group having from 1 to 4 carbon atoms and $R^1$ is hydrogen, methyl, chloro or bromo, the $R^1$ substitution in the compounds of Formula (A) being at the 3, 4 or 5 positions of the furan or thiophene ring.

2. A compound of claim 1 wherein X is oxygen.
3. A compound of claim 1 wherein X is sulphur.
4. A compound of claim 1 wherein R is hydrogen.
5. A compound of claim 1 wherein R is methyl.
6. A compound of claim 2, Formula (A).
7. A carboxylic acid compound of claim 6 wherein R and $R^1$ are both hydrogen, 5-(2-furoyl)-1,2-dihydro-3H-pyrrolo[1,2-a]pyrrole-1-carboxylic acid.
8. An isopropyl ester of the compound of claim 7, isopropyl 5-(2-furoyl)-1,2-dihydro-3H-pyrrolo[1,2-a]-pyrrole-1-carboxylate.
9. A compound of claim 6 wherein R is hydrogen and $R^1$ is methyl.
10. A compound of claim 6 wherein R is hydrogen and $R^1$ is chloro.
11. A compound of claim 6 wherein R is hydrogen and $R^1$ is bromo.
12. A compound of claim 3, Formula (A).
13. A carboxylic acid compound of claim 12 wherein R and $R^1$ are both hydrogen, 5-(2-thenoyl)-1,2-dihydro-3H-pyrrolo[1,2-a]pyrrole-1-carboxylic acid.
14. An ethyl ester of the compound of claim 13, ethyl 5-(2-thenoyl)-1,2-dihydro-3H-pyrrolo[1,2-a]-pyrrole-1-carboxylate.
15. A compound of claim 12 wherein R is hydrogen and $R^1$ is methyl.
16. A compound of claim 12 wherein R is hydrogen and $R^1$ is chloro.
17. A carboxylic acid compound of claim 12 wherein the $R^1$ substitution is at the C-4 position of the thiophene ring, 5-(4-chloro-2-thenoyl)-1,2-dihydro-3H-pyrrolo[1,2-a]pyrrole-1-carboxylic acid.
18. An isopropyl ester of the compound of claim 17, isopropyl 5-(4-chloro-2-thenoyl)-1,2-dihydro-3H-pyrrolo[1,2-a]pyrrole-1-carboxylate.
19. A carboxylic acid compound of claim 16 wherein the $R^1$ substitution is at the C-5 position of the thiophene ring, 5-(5-chloro-2-thenoyl)-1,2-dihydro-3H-pyrrolo[1,2-a]pyrrole-1-carboxylic acid.
20. An isopropyl ester of the compound of claim 19, isopropyl 5-(5-chloro-2-thenoyl)-1,2-dihydro-3H-pyrrolo[1,2-a]pyrrole-1-carboxylate.
21. A compound of claim 12 wherein R is hydrogen and $R^1$ is bromo.
22. A compound of claim 2, Formula (B).
23. The carboxylic acid compound of claim 22 wherein R is hydrogen, 5-(3-furoyl)-1,2-dihydro-3H-pyrrolo[1,2-a]pyrrole-1-carboxylic acid.
24. A compound of claim 3, Formula (B).
25. The carboxylic acid compound of claim 24 wherein R is hydrogen, 5-(3-thenoyl)-1,2-dihydro-3H-pyrrolo[1,2-a]pyrrole-1-carboxylic acid.
26. A sodium, potassium or calcium salt of the compounds according to Formulas (A) or (B) of claim 1.
27. A potassium salt compound of Formula (A) of claim 26 wherein R and $R^1$ are both hydrogen and X is sulfur, potassium-5-(2-thenoyl)-1,2-dihydro-3H-pyrrolo[1,2-a]pyrrole-1-carboxylate.
28. An (l)-acid isomer of Formulas (A) or (B) of claim 1.
29. A compound of claim 28 wherein R and $R^1$ are both hydrogen.
30. The compound of Formula (A) of claim 29 wherein X is sulfur, (l)-5-(2-thenoyl)-1,2-dihydro-3H-pyrrolo[1,2-a]pyrrole-1-carboxylic acid.
31. A sodium, potassium or calcium salt of an (l)-acid isomer of Formulas (A) or (B) of claim 1.
32. The potassium salt compound of Formula (A) of claim 31 wherein R and $R^1$ are both hydrogen, and X is sulfur, potassium (l)-5-(2-thenoyl)-1,2-dihydro-3H-pyrrolo[1,2-a]pyrrole-1-carboxylate.
33. A composition for treating inflammation, pain or pyrexia in mammals consisting essentially of a pharmaceutically acceptable non-toxic excipient and a therapeutically effective amount of the racemic mixture or the (l)-isomer of a compound represented by the formulas:

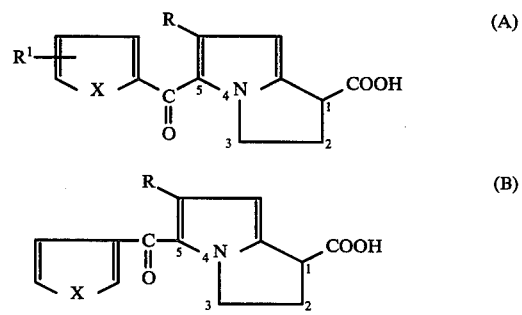

and the pharmaceutically acceptable, non-toxic alkyl esters having from one to 12 carbon atoms and salts thereof, wherein X is oxygen or sulfur, R is hydrogen or a lower alkyl group having from 1 to 4 carbon atoms and $R^1$ is hydrogen, methyl, chloro or bromo, the $R^1$ substitution in the compounds of Formula (A) being at the 3, 4, or 5 positions of the furan or thiophene ring.

34. A method of treating inflammation, pain or pyrexia in mammals which comprises administering to a mammal suffering therefrom a therapeutically effective amount of the racemic mixture or the (l)-isomer of a compound represented by the formulas:

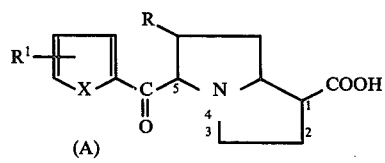

-continued

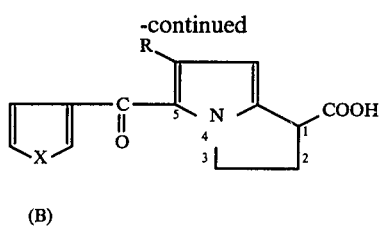

(B)

and the pharmaceutically acceptable, non-toxic alkyl esters having from one to 12 carbon atoms and salts thereof, wherein X is oxygen or sulfur, R is hydrogen or a lower alkyl group having from 1 to 4 carbon atoms and $R^1$ is hydrogen, methyl, chloro or bromo, the $R^1$ substitution in the compounds of Formula (A) being at the 3, 4, or 5 positions of the furan or thiophene ring.

35. A composition for administration to a pregnant mammal to delay onset of parturition consisting essentially of a pharmaceutically acceptable non-toxic excipient and a therapeutically effective amount of the racemic mixture or the (l)-isomer of a compound represented by the formulas:

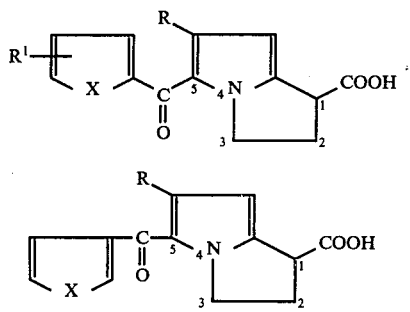

and the pharmaceutically acceptable, non-toxic alkyl esters having from one to 12 carbon atoms and salts thereof, wherein X is oxygen or sulfur, R is hydrogen or a lower alkyl group having from 1 to 4 carbon atoms and $R^1$ is hydrogen, methyl, chloro or bromo, the $R^1$ substitution in the compounds of Formula (A) being at the 3, 4, or 5 positions of the furan or thiophene ring.

36. A method comprising administering to a pregnant mammal to delay the onset of parturition a therapeutically effective amount of the racemic mixture or the (l)-isomer of a compound selected from the group of compounds represented by the formulas:

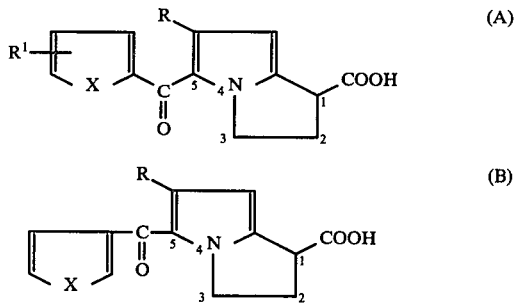

and the pharmaceutically acceptable, non-toxic alkyl esters having from one to 12 carbon atoms and salts thereof, wherein X is oxygen or sulfur, R is hydrogen or a lower alkyl group having from 1 to 4 carbon atoms and $R^1$ is hydrogen, methyl, chloro or bromo, the $R^1$ substitution in the compounds of Formula (A) being at the 3, 4, or 5 positions of the furan or thiophene ring.

37. The method of claim 36 wherein said pregnant mammal is a woman who is not suffering from inflammation, pyrexia, or pain.

38. The method of claim 37 wherein said pregnant woman has had a previous spontaneous abortion, miscarriage or premature delivery, which occurred prior to the time for normal parturition at or about full term.

39. The method of claim 36 wherein said pregnant mammal is a woman who is not suffering from inflammation, pyrexia or nonparturition-causing pain but who is experiencing uterine muscle contractions, said compound being administered in a therapeutically effective amount adapted to reduce the intensity or duration of the uterine muscle contractions, stop the uterine muscle contractions altogether, whereby termination of the pregnancy is postponed from the time it otherwise would have happened.

* * * * *